(12) United States Patent
Billard et al.

(10) Patent No.: US 10,835,345 B2
(45) Date of Patent: *Nov. 17, 2020

(54) END EFFECTOR COUPLER FOR SURGICAL ARM

(71) Applicant: Zimmer Biomet CMF and Thoracic, LLC, Jacksonville, FL (US)

(72) Inventors: Max Holland Billard, Jacksonville, FL (US); Ryan Luby, Ponte Vedra Beach, FL (US); Shawn Robinson, Fleming Island, FL (US); Benjamin Witten, Jacksonville, FL (US); Zachary Frank, Jacksonville, FL (US); Aurelien Bruneau, Jacksonville, FL (US); Catherine Boniface, Jacksonville, FL (US); Saddy Garcia, St. Augustine, FL (US); Robert Carlton, Alexandria, VA (US); Ralph Paul, Alexandria, VA (US); Demetrius Siachames, Alexandria, VA (US); Jeffrey Schlosser, Menlo Park, CA (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 126 days.

This patent is subject to a terminal disclaimer.

(21) Appl. No.: 15/919,161

(22) Filed: Mar. 12, 2018

(65) Prior Publication Data

US 2019/0274778 A1 Sep. 12, 2019

(51) Int. Cl.
*A61B 90/50* (2016.01)
*F16M 11/06* (2006.01)
(Continued)

(52) U.S. Cl.
CPC .... *A61B 90/50* (2016.02); *A61B 2017/00477* (2013.01); *A61B 2090/571* (2016.02); *A61G 13/101* (2013.01); *F16M 11/06* (2013.01)

(58) Field of Classification Search
CPC ......... A61B 90/50; A61B 17/00; A61B 90/57; Y10T 403/595; Y10T 403/602;
(Continued)

(56) References Cited

U.S. PATENT DOCUMENTS 2,752,116 A 6/1956 Minnis
3,910,538 A 10/1975 Baitella
(Continued)

FOREIGN PATENT DOCUMENTS

CN 107614817 A 1/2018
DE 102015104810 A1 9/2016
(Continued)

OTHER PUBLICATIONS

"European Application Serial No. 16773696.6, Extended European Search Report dated Nov. 19, 2018", 8 pgs.
(Continued)

*Primary Examiner* — Tessa M Matthews
(74) *Attorney, Agent, or Firm* — Schwegman Lundberg & Woessner, P.A.

(57) ABSTRACT

An end effector coupler for a surgical arm can include a body, a proximal coupler, and a tool lock. The tool lock can releasably retain a tool stem to the end effector coupler. The tool lock can include a keyed opening, a pin bore, a pin disposed in the bin bore, a biasing element located in the pin bore, and a pin release including an actuator, the pin release operable to retract the pin into to the body to disengage the pin from the tool stem allowing release of the tool stem from the keyed opening.

19 Claims, 23 Drawing Sheets

(51) Int. Cl.
*A61G 13/10* (2006.01)
*A61B 90/57* (2016.01)
*A61B 17/00* (2006.01)

(58) Field of Classification Search
CPC ... Y10T 403/60; F16B 2200/10; F16M 11/06; A61F 13/10
See application file for complete search history.

(56) References Cited

U.S. PATENT DOCUMENTS

| | | | |
|---|---|---|---|
| 4,402,481 | A | 9/1983 | Sasaki |
| 4,514,117 | A | 4/1985 | Scott |
| 5,779,209 | A | 7/1998 | Rello |
| 6,467,362 | B2 * | 10/2002 | Erikson ............. B23Q 5/40 74/424.72 |
| 6,575,653 | B1 | 6/2003 | Kräuter |
| 6,860,877 | B1 | 3/2005 | Sanchez et al. |
| 7,611,378 | B1 | 11/2009 | Brekosky et al. |
| 9,592,096 | B2 | 3/2017 | Maillet et al. |
| D878,585 | S | 3/2020 | Garcia |
| 2002/0017857 | A1 | 2/2002 | Hashimoto et al. |
| 2002/0074472 | A1 | 6/2002 | Gaida et al. |
| 2002/0117857 | A1 | 8/2002 | Eckstein |
| 2002/0177857 | A1 | 11/2002 | Otsuka et al. |
| 2002/0188293 | A1 | 12/2002 | Manzo |
| 2004/0172012 | A1 * | 9/2004 | Otsuka ............. A61B 90/50 606/1 |
| 2010/0020002 | A1 | 1/2010 | Van Woudenberg et al. |
| 2010/0200002 | A1 | 8/2010 | Orban, III et al. |
| 2011/0290855 | A1 | 12/2011 | Moore et al. |
| 2011/0315843 | A1 | 12/2011 | Hung |
| 2012/0182134 | A1 * | 7/2012 | Doyle ............. A61B 1/00149 340/12.22 |
| 2012/0265240 | A1 | 10/2012 | Ganske et al. |
| 2013/0187022 | A1 | 7/2013 | Duportal et al. |
| 2014/0379038 | A1 | 12/2014 | Dogramadzi et al. |
| 2015/0100066 | A1 | 4/2015 | Kostrzewski et al. |
| 2016/0081753 | A1 * | 3/2016 | Kostrzewski ......... A61B 34/25 606/130 |
| 2016/0151120 | A1 | 6/2016 | Kostrzewski et al. |
| 2016/0270780 | A1 | 9/2016 | Hall et al. |
| 2017/0340210 | A1 | 11/2017 | Chuang |
| 2017/0340389 | A1 | 11/2017 | Otto et al. |
| 2017/0360521 | A1 | 12/2017 | Johnson |
| 2018/0116758 | A1 | 5/2018 | Schlosser et al. |
| 2019/0167356 | A1 | 6/2019 | Britton et al. |
| 2019/0274665 | A1 | 9/2019 | Garcia |
| 2019/0274777 | A1 | 9/2019 | Garcia et al. |
| 2019/0274780 | A1 * | 9/2019 | Nowatschin ......... B25J 13/082 |

FOREIGN PATENT DOCUMENTS

| | | |
|---|---|---|
| EP | 2777539 A2 | 9/2014 |
| EP | 2143372 | 12/2014 |
| EP | 3274521 | 1/2018 |
| JP | S57144399 A | 9/1982 |
| JP | S63280911 A | 11/1988 |
| JP | 63280911 A | 11/1998 |
| JP | 2001187064 A | 7/2001 |
| JP | 2018509273 | 4/2018 |
| WO | 9639944 A1 | 12/1996 |
| WO | 2016160272 A1 | 10/2016 |
| WO | 2017017443 | 2/2017 |
| WO | 2017151887 A1 | 9/2017 |
| WO | WO-2019177567 A1 | 9/2019 |
| WO | WO-2019177569 A1 | 9/2019 |
| WO | WO-2019177570 A1 | 9/2019 |

OTHER PUBLICATIONS

"Anatomical Shoulder Fracture System", Zimmer Surgical Technique, 97-4223-003-00 Rev. 1, (2005), 24 pgs.

"Comprehensive Segmental Revision System, Proximal Humeral Reconstruction, Distal Humeral Reconstruction, Total Humeral Reconstruction", Zimmer Biomet Surgical Technique, 0097.1-US-en-REV0416, (2016), 68 pgs.

"Anatomical Shoulder Glenoid", Zimmer Surgical Technique, (2014), 12 pgs.

"International Application Serial No. PCT US2018 022006, Invitation to Pay Additional Fees dated Dec. 12, 2018", 16 pgs.

"U.S. Appl. No. 15/560,894, Restriction Requirement dated Dec. 31, 2018", 7 pgs.

"International Application Serial No. PCT/US2018/021988, International Search Report dated Dec. 20, 2018", 4 pgs.

"International Application Serial No. PCT/US2018/021988, Written Opinion dated Dec. 20, 2018", 6 pgs.

"International Application Serial No. PCT/US2018/022004, Invitation to Pay Additional Fees dated Dec. 19, 2018", 15 pgs.

"3840 Series Holder", Fisso—Rail-mounted instrument holding arm / articulated, [Online]. [Accessed Oct. 16, 2017]. Retrieved from the Internet: <URL: http://www.medicalexpo.com/prod/fisso/product-67723-681104.html>, 3 pgs.

"3D-Arm™", Elekta—Minimally invasive surgery instrument holding arm, [Online]. [Accessed Oct. 16, 2017]. Retrieved from the Internet: <URL: http://www.medicalexpo.com/prod/elekta/product-70692-509376.html>, 8 pgs.

"ALLY Uterine Positioning System", Cooper Surgical, [Online]. [Accessed Oct. 16, 2017]. Retrieved from the Internet: <URL: https://www.coopersurgical.com/Products/Detail/ALLY-Uterine-Positioning-System>, 2 pgs.

"U.S. Appl. No. 15/560,894, Preliminary Amendment filed Sep. 22, 2017", 7 pgs.

"U.S. Appl. No. 15/560,894, Supplemental Preliminary Amendment filed Sep. 29, 2017", 7 pgs.

"ASSISTO Arm System", Geomed GMBH, [Online]. [Accessed Oct. 16, 2017]. Retrieved from the Internet: <URL: http://www.geomed.de/index.php?id=65&L=1>, 1 pg.

"Atlas™ Flex Arm System", Axcess Surgical, [Online]. [Accessed Oct. 16, 2017]. Retrieved from the Internet: <URL: http://www.axcesssurgical.com/axcess-surgical-innovations-products/atlas-flex-arm-system/>, 5 pgs.

"Atlas™ Rigid Arm System", Axcess Surgical, [Online]. [Accessed Oct. 16, 2017]. Retrieved from the Internet: <URL: http://www.axcesssurgical.com/axcess-surgical-innovations-products/atlas-rigid-arm-system/>, 6 pgs.

"Bookler® StrongArm™ Holder", Mediflex, [Online]. [Accessed Nov. 2, 2017]. Retrieved from the Internet: <URL: http://www.mediflex.com/product/bookler-strongarm-holder-and-positioner-set-12-30cm-post/>, (2015), 4 pgs.

"EndoArm", Olympus, [Online]. [Accessed Nov. 2, 2017]. Retrieved from the Internet: <URL: https://www.olympus.co.jp/jp/news/2003b/nr030925endoj.html>, (Sep. 25, 2003), 4 pgs.

"EndoBoy", LUT—Pneumatic Arm, Grecco, 8 pgs.

"EndoCrane", Karl Storz—LEROY Retractors for Laparoscopic Colorectal Surgery, [Online]. [Accessed Oct. 16, 2017]. Retrieved from the Internet: <URL: https://www.karlstorz.com/cps/rde/xbcr/karlstorz_assets/ASSETS/2193800.pdf>, 16 pgs.

"Genzyme Remote Surgical Retractor Arm Hands Free Pneumatic System", Renix International/Alibaba.com Copyright 1999-2017, [Online]. [Accessed Nov. 2, 2017]. Retrieved from the Internet: <URL: http://renix.trustpass.alibaba.com/product/50001078652-219532304/Genzyme_Remote_Surgical_Retractor_Arm_Hands_Free_Pneumatic_System.html>, 2 pgs.

"Helping Hand", Fraunhofer IPA—The helping hand in the operation room Research News, [Online]. [Accessed Oct. 16, 2017]. Retrieved from the Internet: <URL: https://www.fraunhofer.de/en/press/research-news/2015/november/helping-hand-in-the-operation-room.html>, (Nov. 2015), 2 pgs.

"International Application Serial No. PCT/US2016/021076, International Preliminary Report on Patentability dated Oct. 12, 2017", 11 pgs.

"International Application Serial No. PCT/US2016/021076, International Search Report dated Aug. 11, 2016", 4 pgs.

(56) References Cited

OTHER PUBLICATIONS

"International Application Serial No. PCT/US2016/021076, Invitation to Pay Add'l Fees and Partial Search Report dated May 25, 2016", 2 pgs.

"International Application Serial No. PCT/US2016/021076, Written Opinion dated Aug. 11, 2016", 8 pgs.

"IronIntern", Automated Medical, [Online]. [Accessed Oct. 16, 2017]. Retrieved from the Internet: <URL: http://ironintern.com/iron-intern%E2%84%A2>, 1 pg.

"Jarit Endoscope Holder", Integra, [Online]. [Accessed Oct. 16, 2017]. Retrieved from: <URL: https://www.integralife.com/endoscope-instrument-holder-set/product/surgical-instruments-hospitals-surgery-centers-tissue-banks-jarit-laparoscopic-endoscopes-endoscope-instrument-holder-set>, 18 pgs.

"M-Trac", Aesculap / B Braun, [Online]. [Accessed-Oct. 16, 2017]. Retrieved from the Internet: <URL: https://www.bbraun.com/en/products/b/m-trac.html>, 2 pgs.

"Martin's Arm", Hayden Medical (& others), [Online]. [Accessed Oct. 16, 2017]. Retrieved from the Internet: <URL: http://haydenmedical.com/surgical-retractors-martins-arm-retractors/>, 2 pgs.

"Mechanical Arm—Mod. 8470", Ansabere Surgical, [Online]. [Accessed Oct. 16, 2017]. Retrieved from the Internet: <URL: http://www.ansaberesurgical.com/en/productos/brazos-mecanicos/brazo-mecanico-mod-8470/>, 5 pgs.

"Phantom ML", TeDan Surgical Innovations, [Online]. [Accessed Nov. 14, 2017]. Retrieved from the Internet: <URL: http://www.tedansurgical.com/spine/articulating-arms/>, 2 pgs.

"Point Setter", Mitaka Kohki Co., Ltd. Operating / User's Manual MODEL: PSMS2, (Feb. 14, 2010), 28 pgs.

"PositionOR", Surgical Concept Designs, [Online]. [Acessed Nov. 14, 2017]. Retrieved from the Internet: <URL: http://surgical-concepts.com/products/PositionOR/>, 1 pg.

"Postioning Arm", Civco—Laparostat™ Kit, [Online]. [Accessed Oct. 16, 2017]. Retrieved from the Internet: <URL: http://www.civco.com/mmi/resources/ifu/043687.pdf>, 16 pgs.

"SaphLITE | RadLITE", Teleflex Medical, [Online]. [Accessed Nov. 14, 2017]. Retrieved from the Internet: <URL: https://www.teleflex.com/en/usa/prod_saphlite-radlite.php>, 1 pg.

"Saphlite/Saphlift", Genzyme Surgical Products (Jan. 7, 1999), [Online]. [Accessed Oct. 16, 2017]. Retrieved from the Internet: <URL: https://www.accessdata.fda.gov/cdrh_docs/pdf/K990062.pdf>, 5 pgs.

"Speed-Tract", Integra—Table Mounted Speed—Tract Retractor System, [Online]. [Accessedd Oct. 16, 2017]. Retrieved from the Internet: <URL: http://occ.integralife.com/products%2Fpdfs%2Fintegra%20table%20mounted%20speed-tract%20retractor%20system%20brochure.pdf>, 6 pgs.

"Spider2 Limb Positioner", Smith & Nephew, [Online]. [Accessed Nov. 14, 2017]. Retrieved from the Internet: <URL: http://www.smith-nephew.com/new-zealand/advanced-surgical-devices/key-products/sports-medicine/spider2-limb-positioner-for-shoulder--hip--knee--/>, 2 pgs.

"Spine Endoscope & Endoscope Holder", Maxer, [Online]. [Accessed Nov. 2, 2017]. Retrieved from the Internet: <URL: http://www.maxerendoscopy.com/index.php?option=com_content&view=article&id=190:spine-endoscope-endoscope-holder&catid=81:spine-endoscopy&Itemid=858>, (2013).

"SurgiAssist Camera Holder", SurgiToolsMIS, [Online]. [Acessed Nov. 14, 2017]. Retrieved from the Internet: <URL: https://www.surgitools.com/surgiassist-camera-holder.html>, 4 pgs.

"Synaptive BrightMatter Drive Robotic Surgical Video Arm System", Synaptive, [Online]. [Accessed Nov. 14, 2017]. Retrieved from the Internet: <URL: https://www.medgadget.com/2016/05/synaptive-brightmatter-drive-robotic-surgical-videoarm-system.html>, 3 pgs.

"TEE Transducer Holder", Civco, [Online]. [Accessed Oct. 16, 2017]. Retrieved from the Internet: <URL: http://www.civco.com/mmi/resources/product-support/TEE-Holder-Brochure_2008P-2339-Rev-2_low-res-8l9rv5.pdf>, 8 pgs.

"The Freehand System", Freehand—V1.2, [Online]. [Acessed Oct. 16, 2017]. Retrieved from the Internet: <URL: http://freehandsurgeon.com/Products/Detail?id=2>, 3 pgs.

"TiREX® Retractor System", Orion Surgical, [Online]. [Accessed Nov. 2, 2017]. Retrieved from the Internet: <URL: http://www.orion-surgical.com/english/tirex-retractor-system/components-of-the-tirex.html>, (2017), 2 pgs.

"Trimano 3D Support Arm", Maquet, [Online]. [Accessed Nov. 16, 2017]. Retrieved from the Internet: <URL: https://www.maquet.com/int/products/trimano-3d-support-arm/>, 3 pgs.

"UniARM Surgical Support System", Mitaka Kohki Co., Ltd. Operating / User Manual Version 1.1, [Online]. [Accessed Nov. 2, 2017]. Retrieved from the Internet: <URL:http://mitakausa.com/uniarm/>, (Mar. 20, 2009), 19 pgs.

"Unitrac® Pneumatic Holding Arm", Aesculap / B Braun, [Online]. [Accessed Oct. 16, 2017]. Retrieved from the Internet: <URL: https://www.bbraun.com/en/products/b/unitrac-pneumaticholdingarm.html>, 3 pgs.

"Vertek Articulating Arm", Medtronic—Copyright 2013, [Online]. [Accessed Nov. 2, 2017]. Retrieved from the Internet: <URL: http://global.medtronic.com/xg-en/healthcare-professionals/products/neurological/surgical-navigation-imaging/neurosurgery-imaging-surgical-navigation/surgical-procedures.html>, 2 pgs.

"VIKY", Endocontrol Medical, [Online]. [Accessed 2014]. Retrieved from the Internet: <URL: http://www.endocontrol-medical.com/en/viky-en/>, 5 pgs.

"Wingman Scope Holder", Stryker, [Online]. [Accessed Nov. 14, 2017]. Retrieved from the Internet: <URL: http://www.stryker.com/cn/products/OREquipmentTelemedicine/EndoscopicSurgeryEquipment/Laparoscopy/Accessories/ScopeHolder/index.htm#>, 3 pgs.

"U.S. Appl. No. 15/560,894, Response filed Mar. 21, 2019 to Restriction Requirement dated Dec. 31, 2018", 9 pgs.

"European Application Serial No. 18210813.4, Extended European Search Report dated Apr. 12, 2017", 7 pgs.

"U.S. Appl. No. 15/560,894, Non Final Office Action dated May 16, 2019", 9 pgs.

"European Application Serial No. 16773696.6, Response filed Jun. 17, 2019 to Extended European Search Report dated Nov. 19, 2018", 18 pgs.

"Chinese Application Serial No. 201680027778.9, Office Action dated Jul. 12, 2019", w English Translation, 20 pgs.

"U.S. Appl. No. 15/560,894, Response filed Aug. 16, 2019 to Non Final Office Action dated May 16, 2019", 11 pgs.

"Canadian Application Serial No. 3,002,354, Office Action dated Jul. 4, 2019", 4 pgs.

"Unitrac Retraction and holding system for open and minimally invasive surgery", Aesculap Surgical Technologies—Surgical Instruments, (2010), 12 pgs.

"European Application Serial No. 16773696.6, Response filed Jun. 4, 2018 to Office Action dated Nov. 22, 2018".

"International Application Serial No. PCT US2018 022004, International Search Report dated Feb. 14, 2019", 8 pgs.

"International Application Serial No. PCT US2018 022004, Written Opinion dated Feb. 14, 2019", 14 pgs.

"International Application Serial No. PCT US2018 022006, International Search Report dated Feb. 8, 2019", 8 pgs.

"International Application Serial No. PCT US2018 022006, Written Opinion dated Feb. 8, 2019", 15 pgs.

"U.S. Appl. No. 15/560,894, Final Office Action dated Nov. 29, 2019", 8 pgs.

"U.S. Appl. No. 15/918,531, Non Final Office Action dated Sep. 26, 2019", 12 pgs.

"U.S. Appl. No. 29/640,121, Notice of Allowance dated Nov. 5, 2019", 8 pgs.

"Chinese Application Serial No. 201680027778.9, Response filed Oct. 31, 2019 to Office Action dated Jul. 12, 2019", (w/English Claims), 15 pgs.

"Japanese Application Serial No. 2018-501138, Notification of Reasons for Refusal dated Nov. 5, 2019", (w/English Translation), 15 pgs.

"Chinese Application Serial No. 201680027778.9, Office Action dated Feb. 6, 2012", with English translation, 6 pages.

(56) References Cited

OTHER PUBLICATIONS

"U.S. Appl. No. 15/918,531, Response filed Dec. 26, 2019 to Non Final Office Action dated Sep. 26, 2019", 12 pages.
"U.S. Appl. No. 15/919,150, Non Final Office Action dated Jan. 13, 2020", 10 pages.
"U.S. Appl. No. 29/640,121, Corrected Notice of Allowability dated Jan. 21, 2020", 4 pages.
"U.S. Appl. No. 15/560,894, Response filed Jan. 28, 2020 to Final Office Action dated Nov. 29, 2019", 7 pages.
"U.S. Appl. No. 15/560,894, Notice of Allowance dated Feb. 13, 2020", 8 pages.
"U.S. Appl. No. 15/918,531, Notice of Allowance dated Feb. 19, 2020", 11 pages.
"U.S. Appl. No. 15/918,531, Corrected Notice of Allowability dated May 20, 2020", 2 pages.
"U.S. Appl. No. 15/919,150, Response filed Apr. 10, 2020 to Non Final Office Action dated Jan. 13, 2020", 11 pages.
"U.S. Appl. No. 15/919,150, Notice of Allowance dated May 12, 2020", 5 pages.
"U.S. Appl. No. 16/210,787, Restriction Requirement dated Apr. 16, 2020", 5 pages.
U.S. Appl. No. 16/210,787, filed Dec. 5, 2018, Robotic Shoulder Repair and Reconstruction.
"Chinese Application Serial No. 201680027778.9, Response filed Mar. 19, 2020 to Office Action dated Feb. 6, 2020", with English claims, 8 pages.
"Japanese Application Serial No. 2018-501138, Response filed Apr. 22, 2020 to Notification of Reasons for Refusal dated Nov. 5, 2019", with English claims, 15 pages.
"Australian Application Serial No. 2016243292, First Examination Report dated Apr. 7, 2020", 4 pages.
"Canadian Application Serial No. 3,002,354, Office Action dated Apr. 27, 2020", 3 pages.
"Australian Application Serial No. 2016243292, Response filed Sep. 30, 2020 to Subsequent Examiners Report dated Jul. 30, 2020", 30 pgs.
"International Application Serial No. PCT/US2018/021988, International Preliminary Report on Patentability dated Sep. 24, 2020", 8 pgs.
"International Application Serial No. PCT/US2018/022004, International Preliminary Report on Patentability dated Sep. 24, 2020", 14 pgs.
"International Application Serial No. PCT/US2018/022006, International Preliminary Report on Patentability dated Sep. 24, 2020", 15 pgs.

* cited by examiner

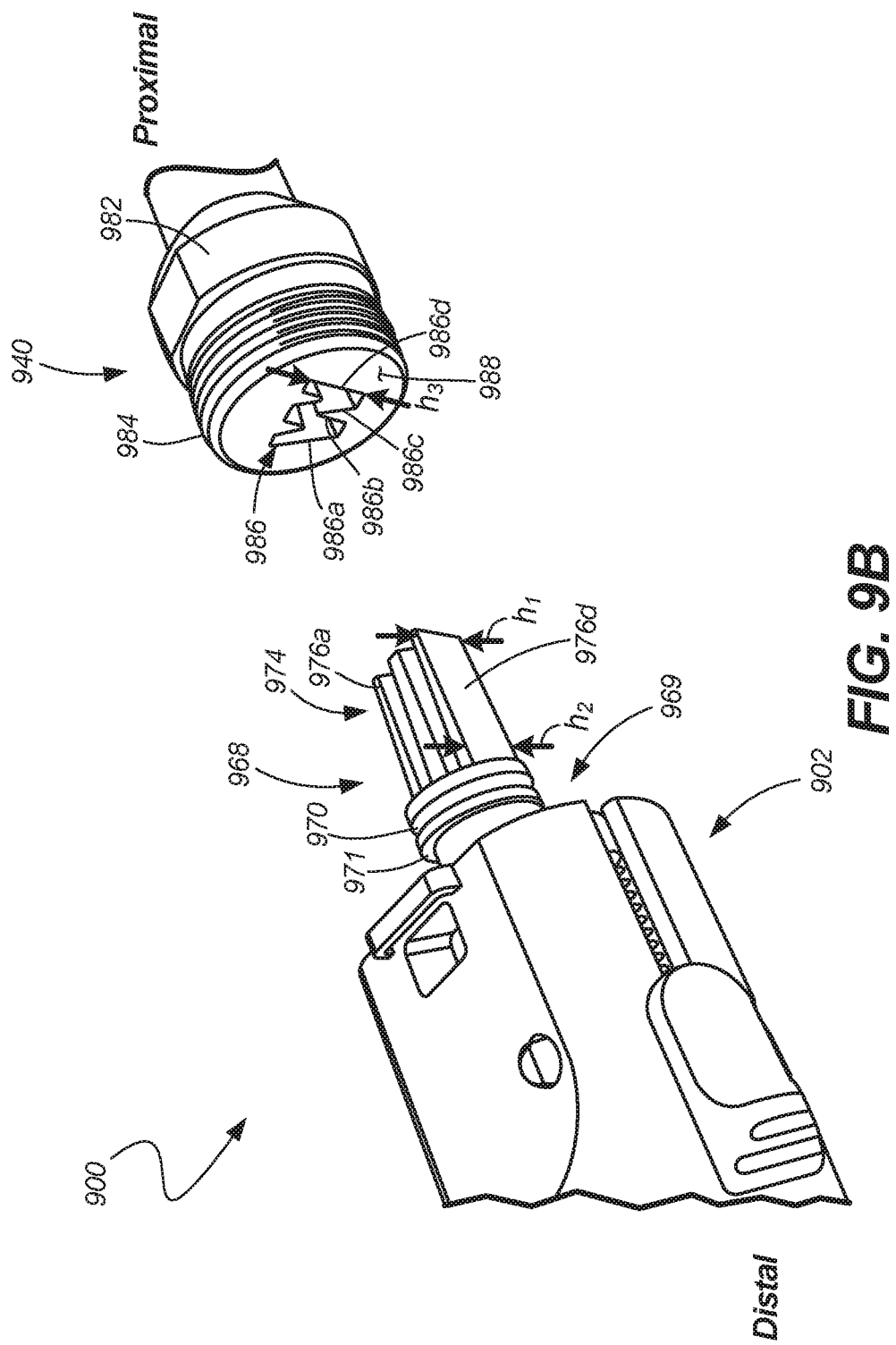

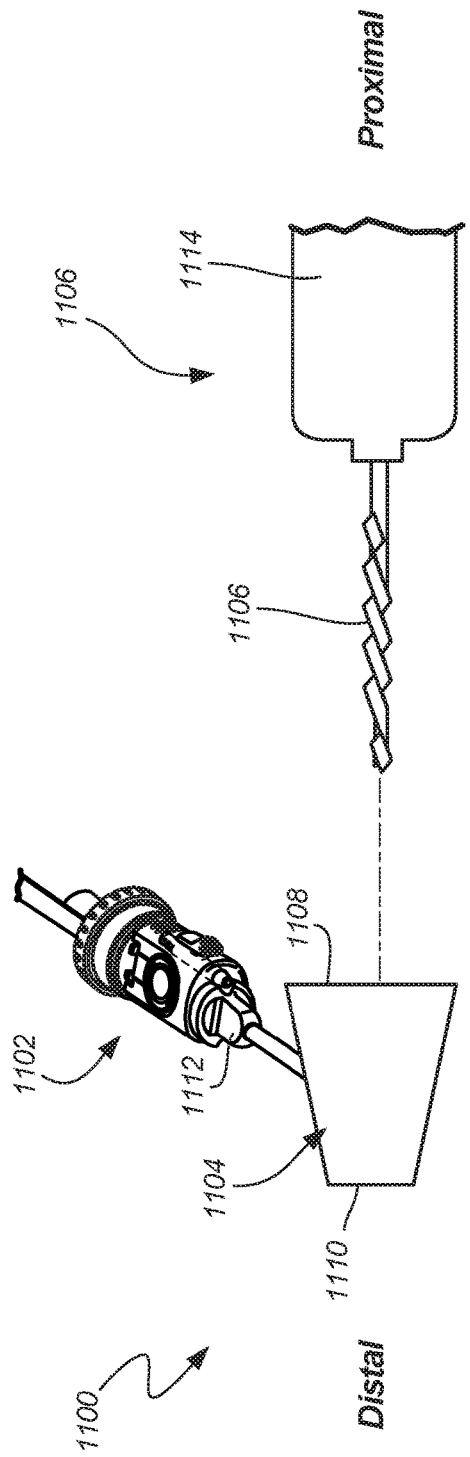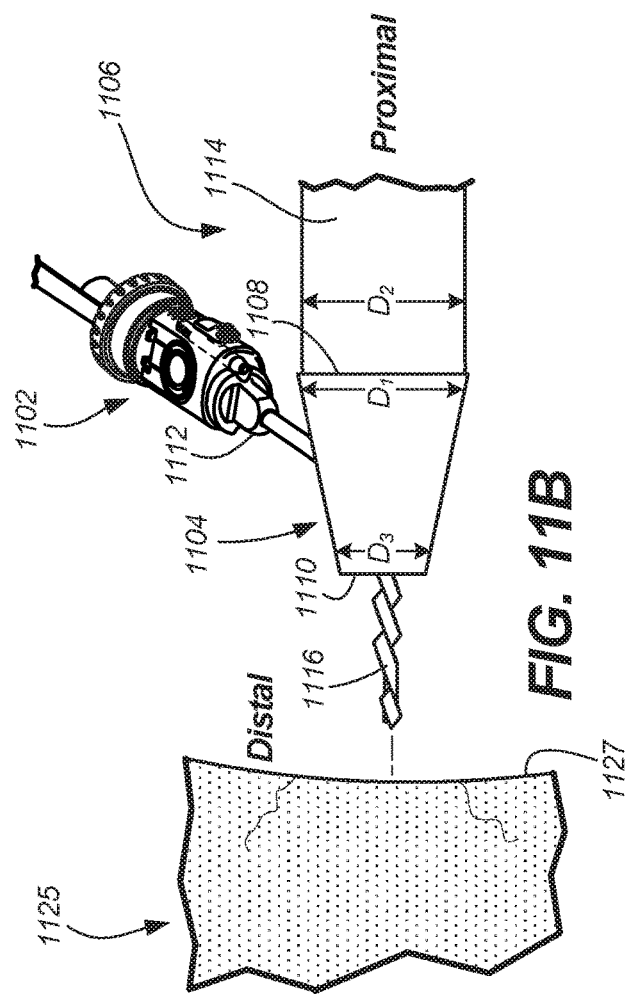
FIG. 11A
FIG. 11B

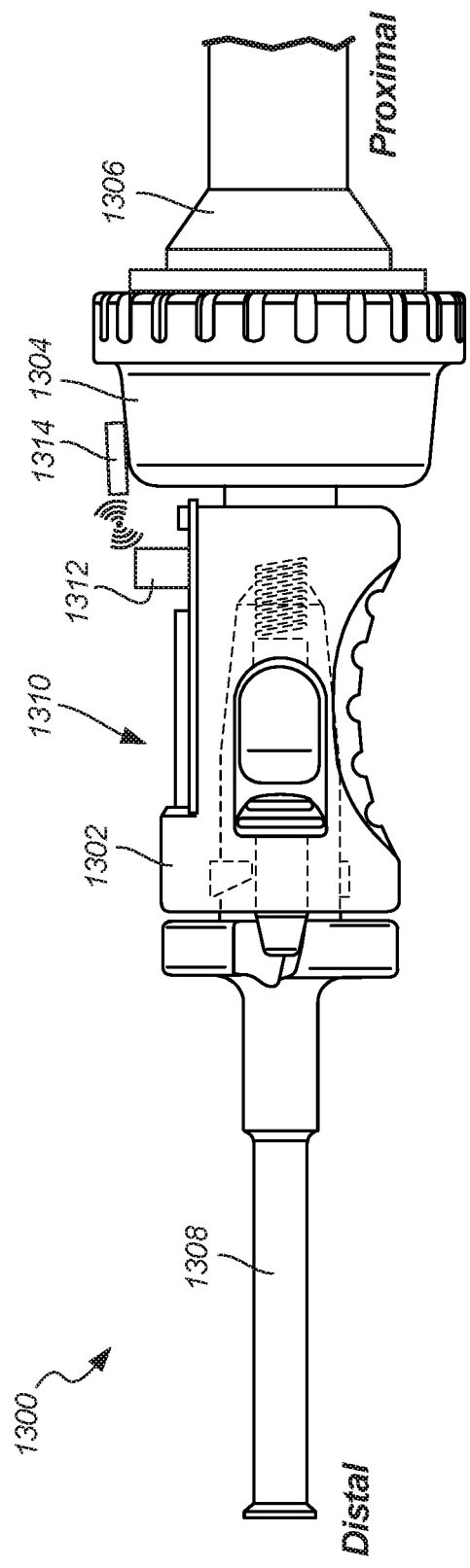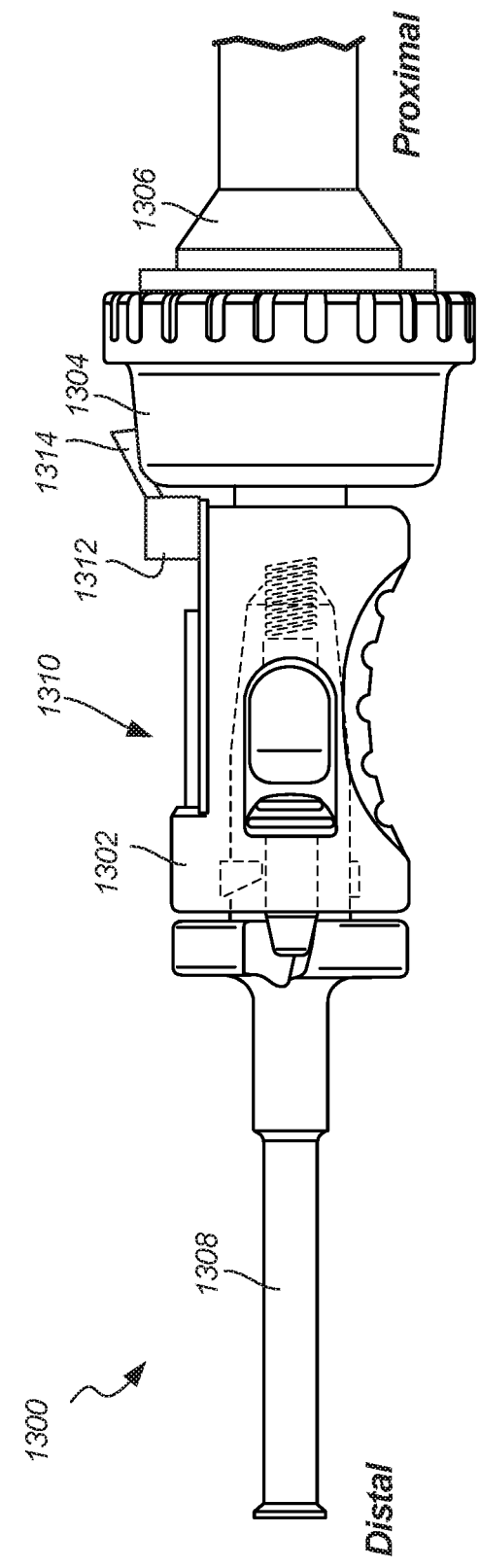

END EFFECTOR COUPLER FOR SURGICAL ARM

BACKGROUND

The present invention relates generally to apparatus and systems for supporting surgical and other instruments. Some surgical procedures include use of a variety of instruments. In some of these procedures, it is required that instruments, such as a retractor, be maintained in a single position for an extended period of time, such as an hour or more. During this time, other instruments can be used to perform other aspects of the surgery. Because it may be difficult or undesirable to manually hold a position of an instrument for such lengths of time, mechanical and/or electromechanical arms can be used to hold the position of the instrument while other aspects of the procedure are performed. Some arms can be adjustable such that a position of the arm can be adjusted before or during the procedure.

CROSS-REFERENCE TO RELATED PATENT DOCUMENTS

This patent application is also related to Jeffrey Schlosser et al., U.S. patent application Ser. No. 15/560,894 entitled "Rapidly Repositionable Powered Support Arm," filed on Sep. 22, 2017 which is hereby incorporated by reference herein in its entirety.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9B illustrates a perspective view of an end effector coupler, in accordance with at least one example of this disclosure.

FIG. 11A illustrates a perspective view of a surgical drill system in a first condition, in accordance with at least one example of this disclosure.

FIG. 11B illustrates a perspective view of a surgical drill system in a second condition, in accordance with at least one example of this disclosure.

FIG. 13A illustrates a perspective view of an end effector coupler, in accordance with at least one example of this disclosure.

FIG. 13B illustrates a perspective view of an end effector coupler, in accordance with at least one example of this disclosure.

DETAILED DESCRIPTION

Figure 1:
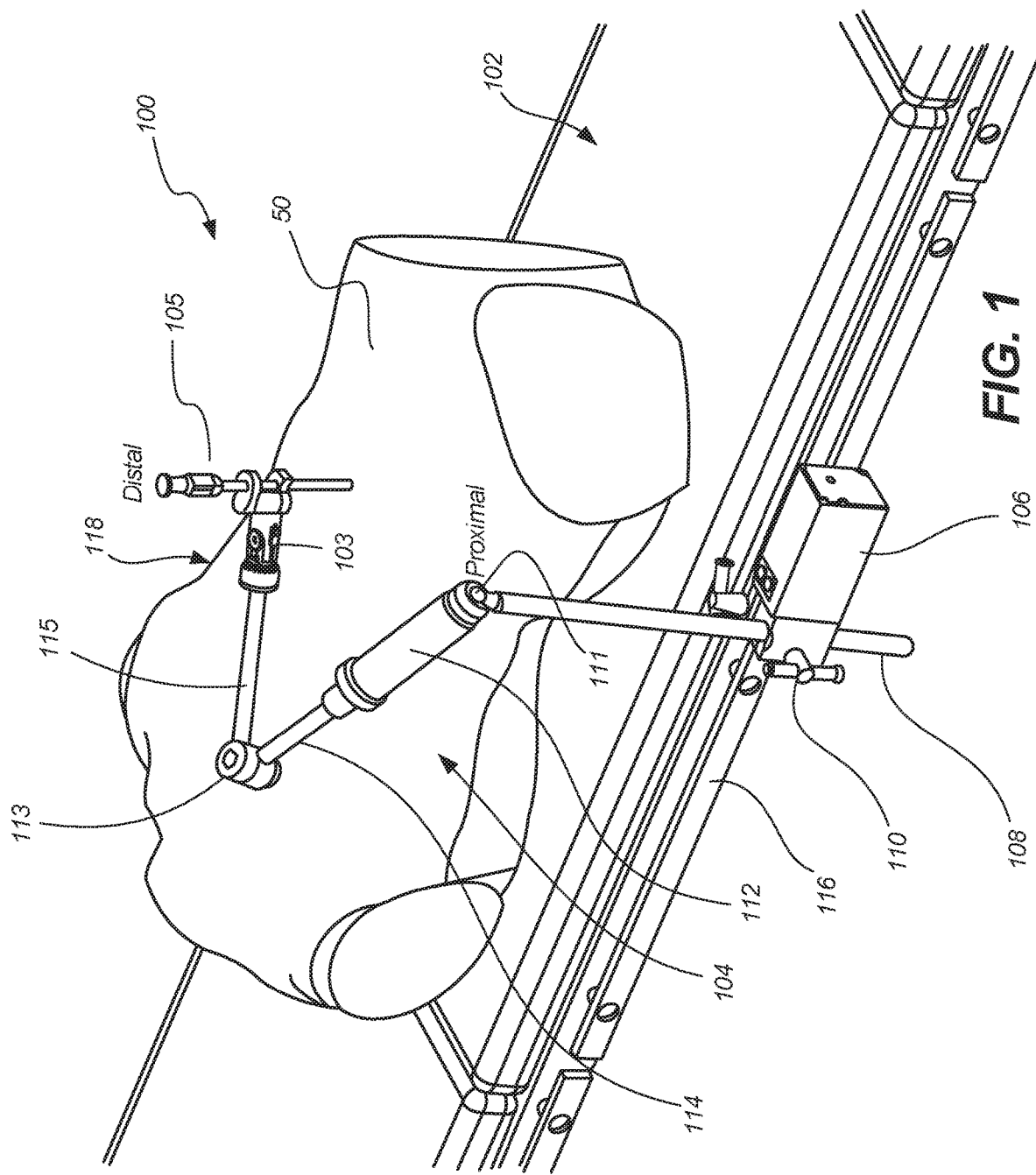
FIG. 1 illustrates a perspective view of a repositionable, lockable surgical arm system, in accordance with at least one example of this disclosure.

Some surgical procedures require a variety of instruments. In some cases, it is desired to hold instruments, such as a retractor, in a single position for an extended period of time, such as an hour or more. In these procedures, adjustable mechanical and/or electromechanical arms are often used to hold the position of the instrument while other aspects of the procedure are performed. One type of arm sometimes employed is an arm that is manually articulable when unlocked and is prevented from being moved when locked. Because these arms are made for use with instruments, there is a need to secure instruments to the arm. And, because a single procedure may require multiple instruments and because the arms may be used for various procedures, there is a need for a method of quickly and easily securing a variety of tools to the arm along with a need for various instruments securable to the arm.

This disclosure provides a solution to these issues through the use of an end effector coupler and various tools coupleable thereto. The coupler can be releasably or fixedly secured to the arm and can include components allowing for tools to be released quickly and easily while providing a secure connection between the tool and the arm. More specifically, the end effector coupler can include a tool lock to secure a tool stem within the end effector coupler. As part of the locking engagement between the end effector and the tool, the tool stem and end effector body can interface in a taper-to-taper arrangement to reduce play or relative movement between the end effector coupler and the tool. Similarly, the end effector body and surgical arm can interface in a taper-to-taper arrangement to reduce play or relative movement between the end effector coupler and the surgical arm.

The end effector can also include a keyed opening and a counterbore coaxial with a central bore of the end effector. The tool stem can also include key bits configured to pass through keyways of the keyed opening to ensure alignment with the end effector, where the key bits also engage a surface between the counter bore and the proximal side of the keyed opening as the tool is rotated; this can draw the stem completely within the end effector to secure the tool thereto.

Also, the locking mechanism can include a retractable pin (operable using an actuator), where the pin can extend from the bore to engage a flange of the stem. This locking engagement can prevent unwanted relative rotation of the tool and stem relative to the end effector coupler, helping to limit unwanted release of the tool from the end effector coupler. When it is desired to remove the tool, the pin can be retracted so that the tool and stem can be rotated for removal from the end effector coupler, allowing for quick release of tools from the end effector coupler. These and other features and benefits are discussed with reference to figures in further detail below.

Further, various tools can be coupleable to the end effector through a common stem. The tools can include: a small instrument holder for coupling small instruments to the surgical arm; a large instrument holder for coupling large instruments to the surgical arm; a flat instrument holder; a scope holder, and more. The end effector coupler can help allow for these various tools to be quickly removed and coupled to the surgical arm so that a variety of tools (and instruments retained by the tools) can be positionable using the arm and operated with the arm.

As used herein, the terms "proximal" and "distal" should be given their generally understood anatomical interpretation. The term "proximal" refers to a direction generally toward the torso of a patient or base or handle of a tool or instrument, and "distal" refers to the opposite direction of proximal, i.e., away from the torso of a patient or toward the working end of the tool.

FIG. 1 illustrates a perspective view of repositionable, lockable surgical arm system 100, in accordance with at least one example of this disclosure. Lockable surgical arm system 100 can include table 102, arm 104, instrument 105, base unit 106, and instrument holder 107. Table 102 can include rail 116. Base unit 106 can include pole 108 and manual clamp 110. Arm 104 can include proximal joint 111, actuator unit 112, distal joint 113, proximal arm 114, distal arm 115, and end effector coupler 118, and lock/unlock button 120. Also shown in FIG. 1 are orientation indicators Proximal and Distal (shown and discussed with respect to the adjustable arm).

Base unit 106, which can include power control circuit components for an electrically powered actuator (such as actuator 112), can be secured to rail 116 of surgical table 102 using, for example, a clamp. Manual clamp 110a of base unit 106 can be operated to tighten base unit 106 against railing 116 and manual clamp 110b can be operated for adjustment of pole 108 to set a height of arm 104 above surgical table 102. Instrument holder 107 can be secureable to a distal end of end effector coupler and can be configured to retain various instruments in a fixed (or adjustable) position relative to arm 104.

Electric actuator unit 112 of arm 104 can be located near a proximal end of arm 104 and can be coupled to pole 108 at proximal joint 111. Electric actuator 112 can also be coupled to a proximal portion of proximal arm 114. Proximal arm 114 can be coupled to electric actuator 112 via a joint or as an actuatable part of actuator 112 in other examples. Distal arm 115 can be coupled to a distal portion of proximal arm 114 via distal joint 113. Effector coupler 118 can connect instrument 105 to the distal end of arm 104. In some examples, lock/unlock button 120 can be provided on or near end effector coupler 118.

The arms of lockable surgical arm system 100 can comprise a serial linkage of arm segments joined by spherical and/or rotational joints. Each of joints 111 and 113 (and any other joints in other examples) can be pivotable and/or rotational joints allowing movement of connected components with one or more degrees of freedom. Joints 111 and 113 (and joints within actuator 112) can be locked and unlocked using base unit 106 and actuator 112, which can be an electric bilateral actuator. In some examples, the joints of the arm can be locked and unlocked with a fluid, pneumatic, or hydraulic system.

While only proximal arm 114 and distal arm 115 are shown in FIG. 1, additional arm segments can be provided between actuator 112 and end effector coupler 118. Each additional arm segment may require one or more additional joints to form a repositionable, lockable support arm structure. Such additional arm segments can provide greater coverage and ability for the arm to be positioned with more degrees of freedom in the surgical field.

In operation of some examples, lock/unlock button 120 can be operable by a user to initiate power locking and unlocking of arm 104. When lock/unlock button 120 is not depressed arm 104 can be in a locked state where joints 111 and 113 are locked such that proximal arm 114 and distal arm 115 cannot move relative to each other or to table 102. When lock/unlock button 120 is pressed, actuator 112 can unlock joints 111 and 113 such that end effector coupler 118 can be positioned, as desired, and as guided by joints 111 and 113 and proximal arm 114 and distal arm 115. That is, end effector coupler 118 can be moved to a desired position relative to body 50 through movement paths limited by the freedom of arm 104 to position instrument 105 to a desired position relative to body 50.

FIG. 2A illustrates a perspective view of surgical arm system 200, in accordance with at least one example of this disclosure. FIG. 2B illustrates a perspective view of surgical arm 200, in accordance with at least one example of this disclosure. FIGS. 2A and 2B are discussed below concurrently.

Figure 2:
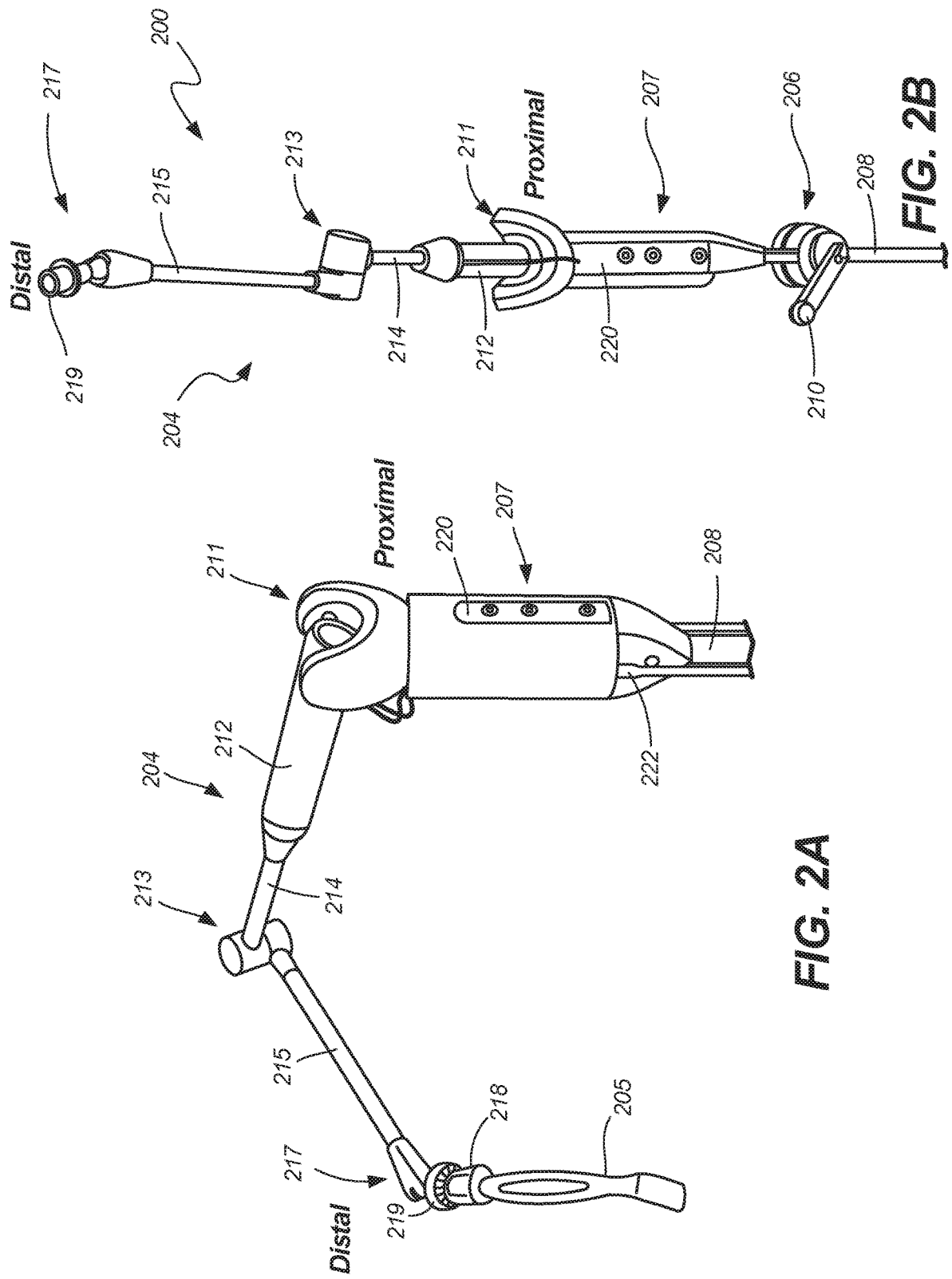
FIG. 2A illustrates a perspective view of a repositionable, lockable surgical arm, in accordance with at least one example of this disclosure.
FIG. 2B illustrates a perspective view of a repositionable, lockable surgical arm, in accordance with at least one example of this disclosure.

Surgical arm 200 can include arm 204, instrument 205, base unit 206 (only shown in FIG. 2B), control device 207, pole 208, and manual clamp 210. Arm 204 can include proximal joint 211, actuator unit 212, distal joint 213, proximal arm 214, distal arm 215, coupler joint 217, end effector coupler 218, and arm coupler 219. Control device 207 can include user interface 220 and can be connected to cable 222. Also shown in FIG. 2 are orientation indicators Proximal and Distal.

Surgical arm 200 can be similar to system 100 discussed above, except that surgical arm 200 can include different features. For example, base unit 206 can be a manually adjustable unit, where manual clamp 210 can be operable to adjust a position of base unit 206 along a rail (e.g., surgical table rail) and to adjust the height of pole 208 (and therefore arm 204). In this example, control device 207 can include electronic components configured to control arm 204. For example, control device 207 can house a controller (discussed further below) and user interface 220, which can include one or more control inputs (such as buttons and switches) and can include audible or visual indicia. Cable 222 can be coupleable to control device 207 to connect a lock/unlock button to control device 207.

Surgical arm 200 can also include arm coupler 219 which can be a distal coupler of arm 204 configured to releasably secure end effector coupler 218 to coupler joint 217 (and therefore to arm 204). In other examples, discussed below, end effector coupler 218 can be fixedly secured to arm 204.

Surgical arm 204 can operate consistently with system 100 described above, except that coupler joint 217 can offer additional range of motion of the embodiment shown in FIG. 1. Further, end effector coupler 218 can be used to quickly and easily remove and secure tools (and therefore instruments), such as tool 205, to surgical arm 204, as discussed in further detail below.

Figure 3:
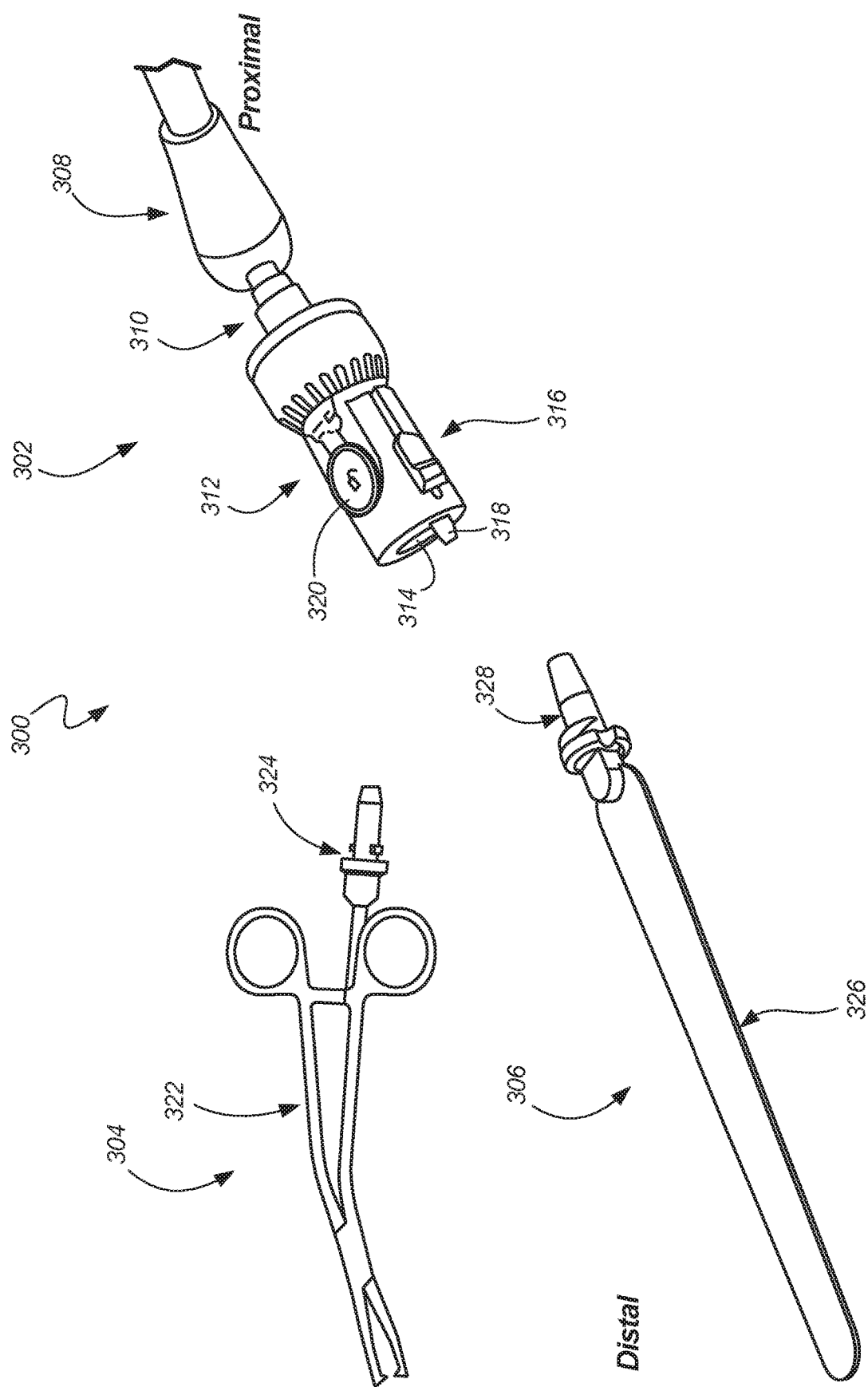
FIG. 3 illustrates a perspective view of a surgical system, in accordance with at least one example of this disclosure.

FIG. 3 illustrates a perspective view of surgical system 300, in accordance with at least one example of this disclosure. End effector system 300 can include arm 302, forceps 304, retractor 306, and lock/unlock button 320. Arm 302 can include distal arm joint 308, arm coupler 310, and end effector coupler 312. End effector coupler 312 can include keyed opening 314, pin release 316, and pin 318. Forceps 304 can include instrument portion 322 and stem 324. Retractor 306 can include instrument portion 326 and stem 328. Also shown in FIG. 3 are orientation indicators Proximal and Distal.

Arm 302 can be consistent with arms 104 and 204 discussed above; however, arm 302 shows additional detail of end effector 312, which can be releasably coupled to distal arm joint 308 via distal coupler 310. End effector coupler 312 can be a coupler configured to releasably secure instruments, such as forceps 304 and retractor 306, to arm 302, and to secure tools, as discussed further in the FIGS. below.

Forceps 304 can be surgical forceps including stem 324 extending from instrument portion 322. Stem 324 can be coupled to instrument portion 322 of forceps 304 such that stem 324 does not interfere with the operation of instrument portion 322 of forceps 304. Retractor 306 can be a substantially flat and/or malleable retractor, such as a ribbon retractor, including stem 328 extending from instrument portion 326 of retractor 306. Stem 328 can be coupled to instrument portion 326 of retractor 306 such that stem 328 does not interfere with the operation of instrument portion 326 of retractor 306. Each of stems 324 and 328 can be of identical structure where each can include tapered stems configured and shaped to be inserted into end effector coupler 312 through keyed opening 314, as discussed in further detail below.

Keyed opening 314 of end effector coupler 312 can include an irregular geometric shape that is sized and shaped to receive each of stems 324 and 328 therethrough to individually secure each of stems 324 and 328 within end effector coupler 312. That is, end effector coupler 312 can secure one stem at a time. Pin 318 of end effector coupler 312 can be disposed within a pin bore of end effector coupler 312 and can extend from a distal end of end effector coupler 312 such that pin 318 can engage a tool stem to help secure the tool stem to the end effector coupler 312. Pin 318 can be coupled to pin release 316, where pin release 316 can be operable to translate pin 318.

Lock/unlock button 320 can be a simple button or switch in some examples and can be in communication with a controller to transmit a signal to lock and unlock the arm.

In operation of some examples, either of stems 324 and 328 can be oriented for insertion and can be inserted into keyed opening 314. Once inserted, the stem can be rotated so that the stem locks into end effector coupler 312 so that a tapered distal end of pin 318 engages an angled (or straight) notch of a collar of the stem to restrict rotation of the stem while within end effector coupler 312. The tool (forceps 304, retractor 306, or other instruments, as discussed below) can then be used in a surgical procedure while connected to end effector coupler 312. And, when lock/unlock button 320 is activated (as discussed in FIGS. 1 and 2 above), end effector coupler 312 and the tool can be positioned as desired (and repositioned) and can be guided by arm 302. Alternatively, the tool can be positioned as desired and then connected to arm 302 when in position.

When the tool is in a desired position, lock/unlock button 320 can be de-activated (or released) to lock a position of arm 302 and therefore of end effector coupler 312 and the instrument (e.g., retractor 306) secured to end effector coupler 312. The instrument can then be used in the desired position and repositioned at any time. When it is desired to remove or change instruments, pin release 316 can be actuated to retract pin 318 so that the tool (and stem 324 or 328) can be rotated within end effector coupler 312 to allow for removal of the stem and tool out of keyed opening 314 and out of end effector coupler 312. This process can be repeated, such that a new tool can be inserted and removed in the same manner.

Figure 4:
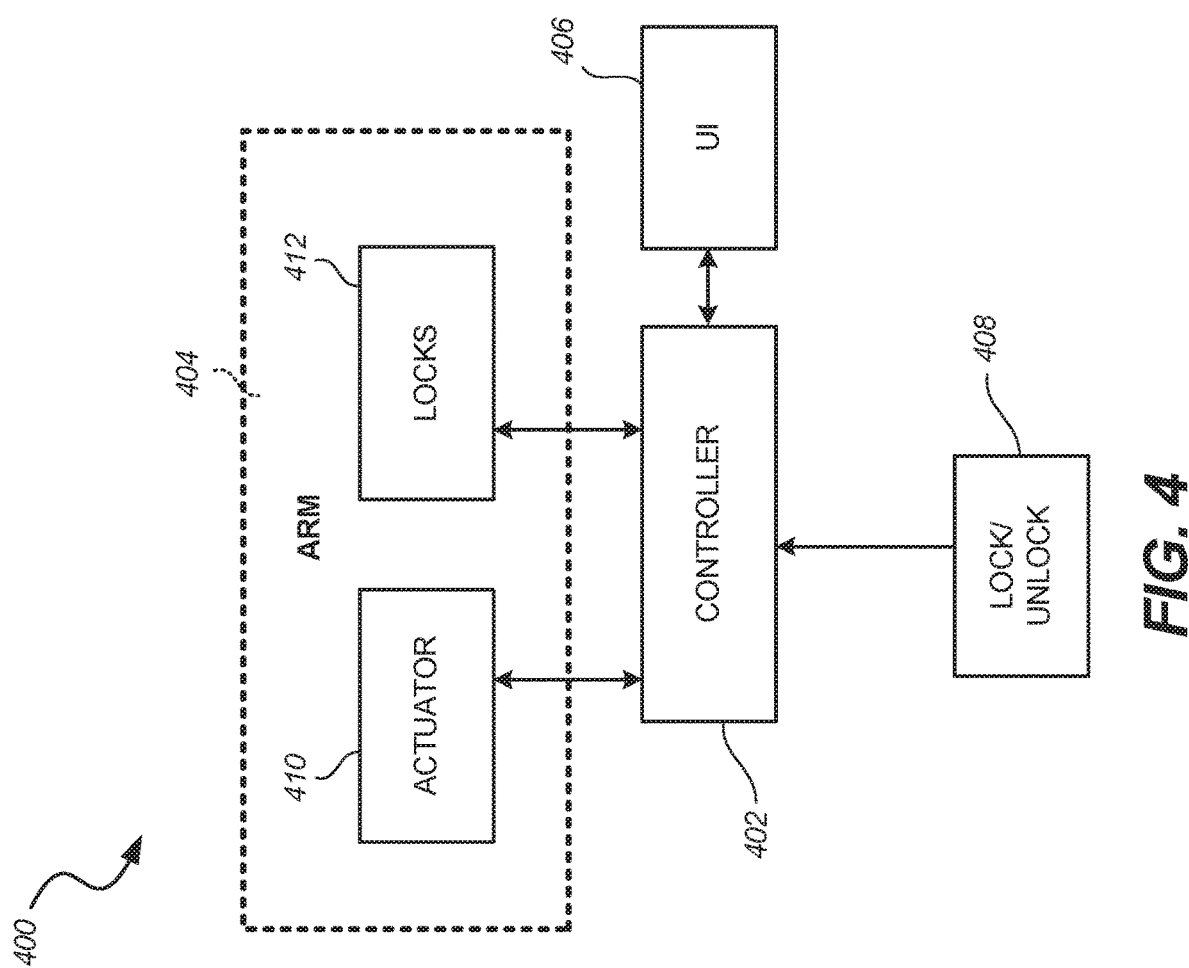
FIG. 4 illustrates a schematic view of a system, in accordance with at least one example of this disclosure.

FIG. 4 illustrates a schematic view of control system 400, in accordance with at least one example of this disclosure. Control system 400 can include controller 402, surgical arm 404, user interface 406, and lock/unlock button 408. Surgical arm 404 can include actuator 410 and lock(s) 412.

Controller 402 can be an electrical and/or electromagnetic control device. Controller 402 can be configured to receive input signals, perform calculations, routines, and analysis, store data, and transmit signals therefrom in response to the calculations, signals, etc. Controller 402 can be a programmable controller, such as a single or multi-board computer, a direct digital controller (DDC), or a programmable logic controller (PLC). In other examples controller 402 can be any computing device, such as a handheld computer, for example, a smart phone, a tablet, a laptop, a desktop computer, or any other computing device including a processor and wireless communication capabilities.

Surgical arm 404 can be similar to the arms discussed above with respect to FIGS. 1-3 in that arm 404 can be a movable arm that is lockable in a desired position. Actuator 410 can be an electric, fluid, or gas-powered actuator in communication with controller 402 and can be operable to translate or otherwise move one or more components (such as an armature) in response to a control signal. Actuator 410 can be physically coupled to locks 412 which can be mechanical or electro-mechanical locks coupled to joints or arms of arm 404. In other examples, actuator 410 can be omitted and locks 412 can be individually operable in response to individual or shared control signals from controller 402.

Control system 400 can optionally include user interface 406 that can be in communication with controller 402. In another example, user interface 406 can be separate from control system 404 or can be communicatively coupled to control system 404.

Lock/unlock button 408 can be a simple button or switch in some examples and can be in communication with controller 402. In some examples, button 408 can be attached to a portion of arm 404. In other examples, button 408 can be attached to other components, such as table 102 of FIG. 1 or can be located on a floor and can be operated as a foot pedal or switch. In some examples, button 408 can be attached to a limb of a patient (for example using an adhesive), such as the limb being operated on. In other examples, a controller may not be present and lock/unlock button 408 can be in direct communication with actuator 410 and/or locks 412.

User interface 406 can be any display and/or input device. For example, user interface can be a monitor, keyboard, and mouse in one example. In other examples, user interface 406 can be a touch screen display. In yet another example, user interface 406 can provide lights, buttons, and/or switches. Controller 402 and user interface 406 can include machine readable medium. The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

In operation of some examples, a user can interact with user interface 406 to power on control system 400. Power can be indicated by a light, for example, on user interface 406 and/or on arm 404. The user can then operate button 408 to send an unlock signal to controller 402 to initiate power locking and unlocking of arm 404. In response, controller 402 can send a signal to actuator 410 and/or locks 412 to unlock locks 412. Once arm 404 is unlocked, the user can move a tool (and instrument) and arm 404 to a desired location and orientation relative to a patient. When the user releases the lock/unlock button, it can send a lock signal (or can cease sending an unlock signal) to controller 402. In response, controller 402 can send a signal (or can cease sending an unlock signal) to actuator 410 and/or locks 412 to lock the joints of arm 404, locking arm 404 in the desired position such that the joints of arm 404 cannot articulate and the end effector of arm 404 cannot move relative to arm 404.

Though the components of control system 400 are shown as being wired to controller 402, the lines of FIG. 4 connecting components of control system 400 can also represent wireless communication paths where each component can communicate using wireless (electromagnetic signals) through protocols such as WiFi, Bluetooth (Bluetooth LE), Near-Field Communications (NFC), and the like.

Figure 5:
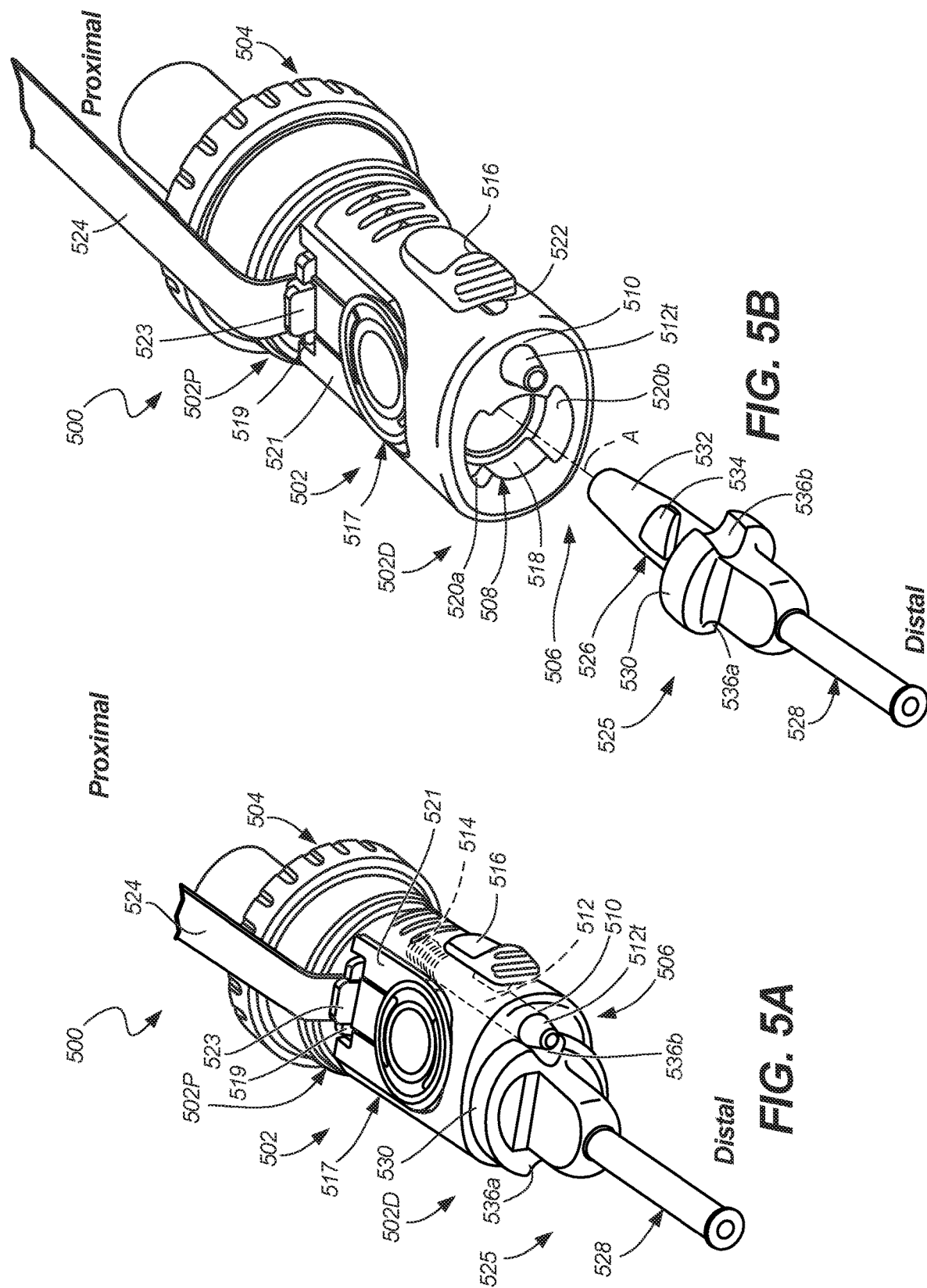
FIG. 5A illustrates a perspective view of an end effector coupler in a first condition, in accordance with at least one example of this disclosure.
FIG. 5B illustrates a perspective view of an end effector coupler in a second condition, in accordance with at least one example of this disclosure.

FIG. 5A illustrates a perspective view of end effector coupler 500 in a first condition, in accordance with at least one example of this disclosure. FIG. 5B illustrates a perspective view of end effector coupler 500 in a second condition, in accordance with at least one example of this disclosure. FIGS. 5A and 5B are discussed below concurrently.

End effector coupler 500 can include body 502, proximal coupler 504, and tool lock 506. Tool lock 506 can include keyed opening 508, pin bore 510, pin 512 (including tapered portion 512$t$), biasing element 514, pin release 516, button 517, and cable 524. Keyed opening 508 can include central bore 518 (or stem opening) and keyways 520$a$ and 520$b$. Body 502 can also include catch 519, flat surface 521, and slot 522. Button 517 can include tab 523. Also shown in FIGS. 5A and 5B is tool 525, which can include stem 526, tool portion 528, and flange 530. Stem 526 can include tapered portion 532 and projections 534 (or key bits 534). Flange 530 can include notches 536$a$ and 536$b$. Also shown in FIGS. 5A and 5B are orientation indicators Proximal and Distal and Axis A.

Body 502 can be a rigid or semi-rigid body comprised of materials such as metals, plastics, foams, elastomers, ceramics, composites, and combinations thereof. Body 502 can include proximal portion 502P and an opposite distal portion 502D including a distal end. Body 502 can be sized and shaped to be handheld and hand-positioned. For example, body 502 can be ergonomically shaped and can include ridges or crenulations to promote ergonomics and grip. Slot 522 of body 502 can be an axially extending slot along a side of body 502 adjacent pin bore 510 and can be sized to allow a portion of pin release 516 to extend through body 502 to couple to pin 512.

Flat surface 521 can be an outer surface of body 502 that is substantially planar or flat and is sized to receive button 517 thereon. Catch 519 can extend outward from flat surface 521 proximate a proximal end of flat surface 521.

Button 517 can be a simple button or switch in some examples and can be connected to a controller through cable 524 to transmit a signal to lock and unlock the arm. Tab 523 can be a locking tab configured to elastically deflect (like a spring) and can include a projection configured to engage catch 519 to secure button 517 to body 502. Cable 524 can be a communication and/or power cable connected to button 517 and to a controller (such as controller 402 of FIG. 4). Cable 524 can be several types of communication cable such as shielded twisted pair (STP), unshielded twisted pair (UTP), fiber optic cable, ethernet cable, coaxial cable, or a patch cable, and the like. In some examples, cable 525 can pass through catch 523 to connect to button 517. In other examples, a wireless component, such as a Bluetooth chip, can be installed at distal end of a surgical arm and can be in electronic communication with button 517, such that the chip can send wireless signal to a controller.

Proximal coupler 504 can be a rigid or semi-rigid body comprised of materials such as metals, plastics, foams, elastomers, ceramics, composites, and combinations thereof. Proximal coupler 504 can have a substantially hollow cylindrical geometric shape and can be securable to distal portion 502D of body 502. In some examples, proximal coupler 504 can include a threaded portion configured to secure proximal coupler 504 to a surgical arm.

Tool lock 506 can be comprised of multiple components of end effector coupler 500 and can be configured to secure tool 525 to end effector coupler 500. Keyed opening 508 of tool lock 506 can be a central bore 518 of keyed opening 508 configured to receive a tool stem therein. Central bore 518 can be a longitudinal bore extending into body 502 from the distal end of distal portion 502D of body 502. Central bore can extend into body 502 along axis A, which can be central to keyed opening 508 and central to body 502 in some examples, but can be offset from a central axis of body 502 in other examples. In some examples, central bore 518 can be sized to receive tool stem 526 in a taper-to-taper arrangement, as discussed further below.

Keyways 520a and 520b can be notches extending radially from central bore 518 and can be sized and shaped to receive key bits 534 of tool 525 when key bits 534 are aligned with keyways 520a and 520b, but can prevent passage of key bits 534 into or out of keyways 520a and 520b (therefore preventing stem from being inserted into keyed opening 508 or being removed therefrom) when key bits 534 are not aligned with keyways 520a and 520b. As discussed further below, each of keyways 520a and 520b can include a proximal face, where each proximal face is engageable with key bits 534 of tool 525.

Pin bore 510 can be a longitudinal bore extending into body 502 from the distal end of distal portion 502D of body 502. In some examples, pin bore 510 can be adjacent (i.e., proximate or near) central bore 518 and can extend through body 502 substantially parallel to central bore 518 and axis A, but can be not parallel to central bore 518 in other examples.

Pin 512 can be a rigid or semi-rigid body comprised of materials such as metals, plastics, foams, elastomers, ceramics, composites, and combinations thereof. Pin 512 can include tapered portion 512t at a distal termination of pin 512. Pin 512 can be disposed within pin bore 510 such that tapered portion 512t extends from pin bore 510 (and therefore beyond distal portion 502D of body 502) when pin 512 is in an extended or locked position.

Biasing element 514 can be a resilient element such as a spring. In some examples, biasing element 514 can be a compression coil spring. In other examples, biasing element can be other springs or resilient members, such as a wave spring or compressible and resilient members comprised of materials such as rubbers, plastic, and the like. In some examples, biasing element can be disposed within pin bore 510 to engage a proximal termination of pin bore 510 and to engage a proximal termination of pin 512, such that biasing element 514 biases pin 512 distally relative to body 502. Pin release 516 can be an actuator operable by hand or tool and can be coupled to pin 512 through slot 522 of body 502.

Tool 525 can be a surgical instrument such as forceps or a retractor (as described below), or various other surgical instruments that can be adapted to include a stem. Stem 526 can be a keyed stem, shaped and sized to be inserted within end effector coupler 500 to secure tool 525 to end effector coupler 500. Tool portion 528 can be connected and/or integral to the operable tool, such as the forceps or retractor. Flange 530 can be a flange or collar extending radially outward from stem and can include notches 536a and 536b extending substantially axially therethrough (though notches 536a and 536b can extend through flange 530 at an axis not parallel with the axis of stem 526, in some examples).

Stem 526 can also include tapered portion 532, which can be sized and shaped to extend into central bore 518 of keyed opening 508, where stem 526 can be tapered to mate with a tapered bore of body 502. Key bits 534 of stem 526 can be projections extending radially outward from stem 526 and key bits 534 can be sized and shaped to pass through keyways 520a and 520b when key bits 534 are aligned with keyways 520a and 520b. Key bits 534 can also be used to secure stem 526 within central bore 518 as discussed further below.

Figure 7:
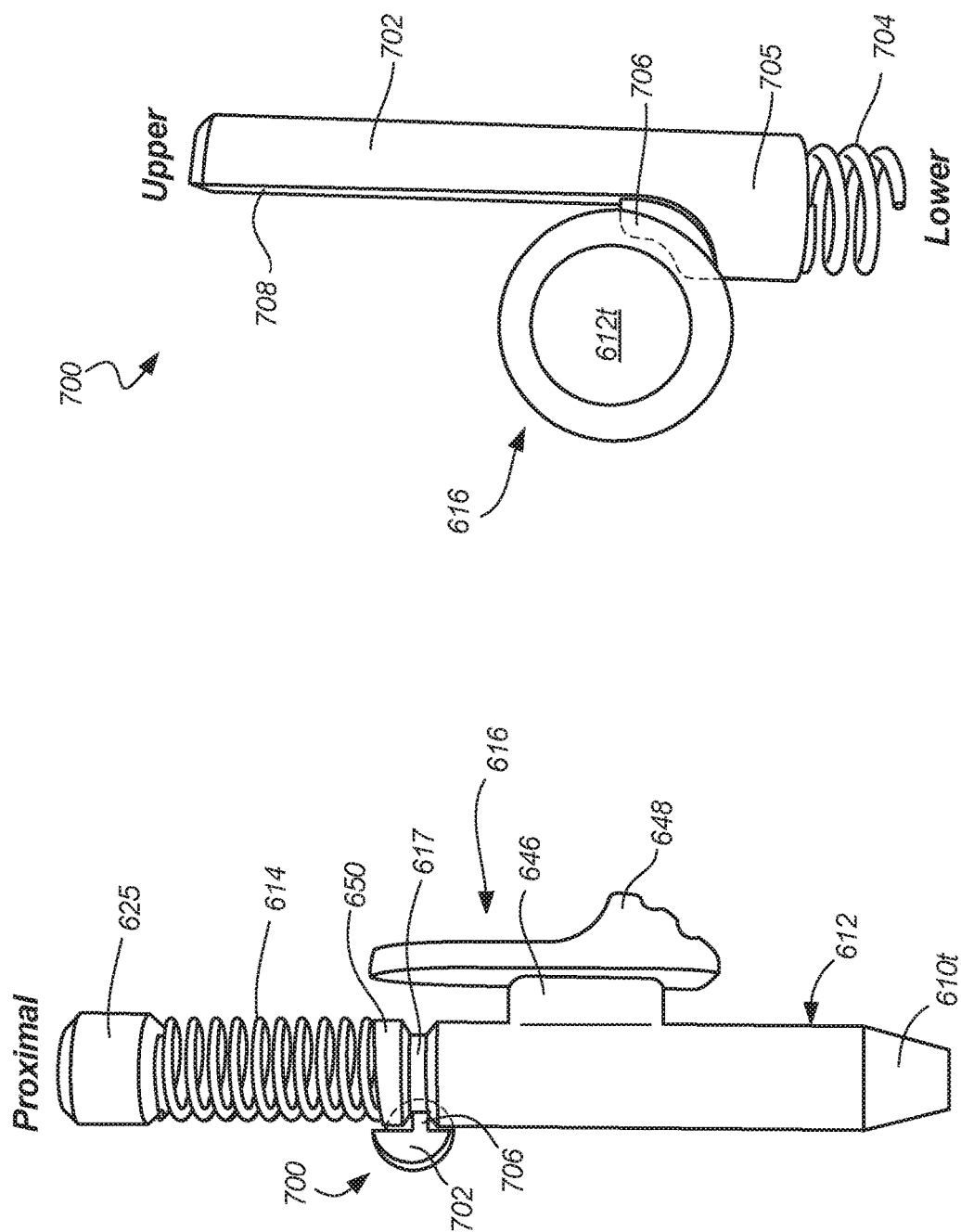
FIG. 7A illustrates a top view of a component of an end effector coupler, in accordance with at least one example of this disclosure.
FIG. 7B illustrates a proximal view of a component of an end effector coupler, in accordance with at least one example of this disclosure.

In operation of some examples, tool 525 can be separate from end effector coupler 500, as shown in FIG. 5B. When it is desired to secure tool 525 to end effector coupler 500, tool stem 526 can be inserted into central bore 518 and rotated clock-wise approximately one quarter of a turn to secure tool 525 to end effector coupler 500. In other examples, tool 525 (and stem 526) can be rotated less than a quarter turn, when additional keyways are included (as discussed below in FIG. 7), and greater than a quarter turn when only one keyway is used.

More specifically, tool stem 526 can be inserted into central bore 518 until key bits engage body 502. Key bits 534 can then be aligned with keyways 520a and 520b to allow tool stem 526 to be further inserted into central bore 518. As discussed further below, tool stem 526 can then be rotated clockwise (from a distal perspective) to seat key bits 534 within a counterbore of central bore 518, where contact between key bits 534 and portions of central bore 518 draw tool stem 526 completely into central bore 518 as stem 526 is rotated. In other examples, tool stem 526 can be rotated counter-clockwise to seat key bits 534 within the counter-bore of central bore 518.

Alternatively, tool stem 526 can be inserted into central bore 518 until key bits engage body 502. Key bits 534 can then be aligned with keyways 520a and 520b to allow tool stem 526 to be further inserted into central bore 518 entirely until key bits 534 rest within a counter bore of central bore 518 which extends stem 526 entirely into central bore 518. Tool stem 526 can then be rotated clockwise (from a distal perspective) to seat key bits 534 within the counterbore of central bore 518.

During insertion of tool stem 526 into central bore 518, a proximal portion of flange 530 can contact pin 512 to cause pin 512 to move proximally into pin bore 510. As tool stem 526 is rotated, one of notches 536a and 536b will align with tapered portion 512t of pin 512 as key bits 534 draw tapered portion 532 into central bore 518, allowing pin 512 to extend from pin bore 510 and into either notch 536a or notch 536b. Pin 512 can automatically extend to this extended position due to being biased to extend distally from pin bore 510 by biasing element 514. When pin 512 is in this position, pin 512 can apply a force from biasing element 514 on flange 530 to further ensure a stable connection between tool 525 and end effector coupler 500. Also, as pin 512 engages one of notches 536a and 536b, the interaction can produce a noise in addition to being visible through one of notches 536a or 536b, which can provide indications to an operator that tool 525 is secured to end effector coupler 500.

The taper-to taper interface of stem 526 with central bore 518 and the engagement of key bits 534 with a proximal portion of keyed opening 508 and the counterbore of central bore 518 can both help limit undesired movement of tool 525 relative to end effector coupler 502; and, the engagement of flange 530 with pin 512 can help limit counter-clockwise rotation of tool 525 relative to central bore 518 and body 502 to help prevent back-out of tool 525 from end effector coupler 500, securing tool 525 to end effector coupler 502. In some examples, during insertion of stem 526 into central bore 518, contact between taper-to taper interface of stem 526 with central bore 518 can occur substantially simultaneously as the engagement of key bits 534 with a proximal portion of keyed opening 508 and substantially simultaneously as the engagement of flange 530 with pin 512 so that stem 526 is secured in all directions relative to end effector coupler 502 all at once.

Also, because tapered portion 512*t* is tapered and because notches 536*a* and 536*b* can be angled, tapered portion 512*t* can contact a large surface area of either one of notches 536*a* and 536*b*. This contact can further help limit unwanted back-out of tool 525 from end effector coupler 500. All of these features that help secure tool 525 to end effector coupler 500 can provide a wear resistant design for the application where users frequently change instruments for different procedures.

When tool 525 is secured to end effector coupler 500, lock/unlock button 517 can be operated (or pressed) to unlock the surgical arm to which end effector coupler 500 is secured. The end effector coupler 500 and tool 525 can then be positioned as desired while lock/unlock button 517 is pressed. Then, when a desired position is obtained, lock/unlock button 517 can be released to lock the joints of the surgical arm, holding the desired position of end effector coupler 500 and tool 525.

When it is desired to remove tool 525 from end effector coupler 500, pin release 516 can be translated proximally, where slot 522 guides and limits translation of pin release 516. Proximal retraction of pin release 516 can retract pin 512 into pin bore such that pin 510 is no longer engaging a notch (of notches 536*a* and 536*b*), as shown in FIG. 6B. This allows a user to rotate tool 525, along with stem 526 and flange 530, counter-clockwise so that key bits 534 can be disengaged from the distal side of keyed opening 508 and can move out of the counterbore and into alignment with keyways 520*a* and 520*b* of central bore 518, allowing stem 526 to be removed from central bore 518. Because pin release 516 can be easily actuated by hand and rotation of stem 526 requires about a quarter turn of tool 525 with little resistance, tool 525 can be easily and quickly removed from end effector coupler 500.

Figure 6:
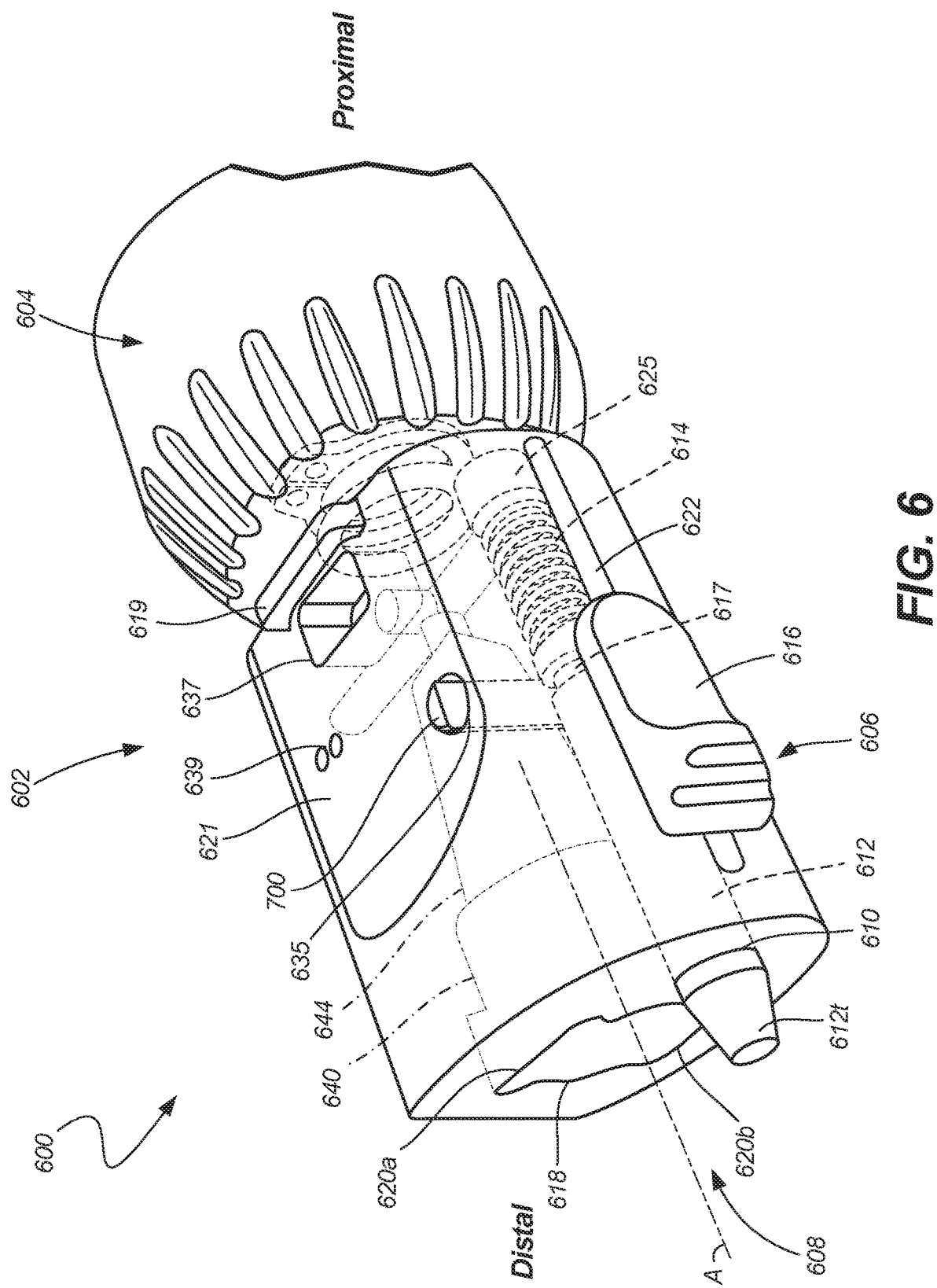
FIG. 6 illustrates a perspective view of an end effector coupler, in accordance with at least one example of this disclosure.

FIG. 6 illustrates a perspective view of end effector coupler 600, in accordance with at least one example of this disclosure. In this example, the end effector coupler can include an interface for receiving a control device, such as a button. In some examples, the end effector coupler can include a lock interactive with the button to help prevent securing of improper tools to the end effector coupler. Any of the previously discussed end effectors can include similar structures to support an interface for a control device and a lock.

End effector coupler 600 can include body 602, proximal coupler 604, tool lock 606, and lock 700. Tool lock 606 can include keyed opening 608, pin bore 610, pin 612 (including tapered portion 612*t*), biasing element 614, and pin release 616. Pin 612 can include groove 617 and can be adjacent to stopper 625. Keyed opening 608 can include central bore 618 (or stem opening), keyways 620*a* and 620*b*, counterbore 640, and bore taper 644. Body 602 can also include catch 619, flat surface 621, lock bore 635, notch 637, terminals 639, and slot 622. Also shown in FIG. 6 are orientation indicators Proximal and Distal and Axis A.

As shown in FIG. 6, body 602 provides an interface to receive a button, for example button 517 of FIGS. 5A and 5B. The button can be secured to flat surface 621 of body 602 through an interface using a tab of the button. A projection of the tab can be lockingly engaged with catch 619 and can be partially inserted into body 602 through tab channel 637. As discussed above, tab 523 can be configured to elastically deflect (like a spring). When it is desired to remove button 617 from body 602, tab 523 can be moved (or deflected) distally to release tab 523 from catch 619 so that tab 523 can be removed from tab channel 637, allowing button 517 to be removed from end effector coupler 600. Though tab channel 637 is shown as extending into body 602 from flat surface 621 near a proximal side of catch 619, tab channel 637 can be located in any position relative to catch 619 and can be omitted entirely in other examples. Similarly, catch 619 can be positioned in various locations around flat portion 621 of body 602.

FIG. 6 also shows terminals 639, which can be electrical contacts or connections configured to electrically couple to a button, such as button 517, when the button is secured to flat surface 621. FIG. 6 shows two terminals, but in some embodiments, additional terminals may be positioned on body 602, such as on flat surface 621, and one or more corresponding terminals or conducting elements may be found on the underside of button 517. In some examples, terminals 639 can connect to wires or conductors within body 602 that can be electrically connected to a surgical arm and ultimately a controller, such as surgical arm 404 and controller 402. In some examples, the wires or conductors within body 602 can be rated for autoclaving. In some examples, the button can also be integral to end effector coupler 600 and rated for autoclaving processes. In operation, a user may depress button 517, which completes an electrical circuit between terminals 639, thereby sending an unlock signal (via wires or conductors within body 602, for example) to surgical arm 404 and/or controller 402 to unlock the joints of surgical arm 404. Releasing the button 517 from its depressed state causes the electrical circuit between terminals 639 to be broken, thereby ceasing to send an unlock signal (via wires or conductors within body 602, for example) to surgical arm 404 and/or controller 402, such that the joints of surgical arm 404 are locked again.

FIG. 6 also shows lock bore 635, which can be a bore extending from flat surface 621 into body 602. Lock bore 635 can intersect with pin bore 610 within body 602, where lock bore 635 can be substantially transverse to pin bore 610. Lock 700 can be a semi-rigid or rigid member that can be disposable in lock bore 635 to interact with pin 612 to function as a mechanical lock. In some examples, lock 700 can be biased by a spring or biasing element (discussed in FIGS. 7A and 7B below) to bias lock 700 to extend beyond flat surface 621 of body 602. When lock 700 is in the extended position, a portion of lock 700 can interface with pin groove 617 to restrict translation of pin 612 relative to body 602. When pin 612 is not free to translate, pin 612 cannot retract to receive a flange of a tool stem (e.g., flange 530), and a tool cannot be secured to end effector coupler 600.

When a button (such as button 517 of FIG. 5A) is secured onto flat portion 621, the button can contact lock 700 and can overcome the spring force and can translate lock 700 into lock bore 635 to disengage lock 700 from pin groove 617, so that pin 612 can freely translate within pin bore 610. When lock 700 is in the retracted position, a tool can be secured to end effector coupler 600. In this way, lock 700 provides a way to help prevent misuse of end effector coupler 600.

FIG. 6 also shows stopper 625, which can be a plug or stop disposable in a proximal portion of pin bore 610 in a fixed position therein. Stopper 625 can be configured to engage a distal portion of biasing element 614 to allow biasing element 614 to bias pin 612 to extend distally from pin bore 610.

FIG. 7A illustrates a top view of pin 612 and lock 700, in accordance with at least one example of this disclosure. FIG. 7B illustrates a proximal view of pin 612 and lock 700, in accordance with at least one example of this disclosure. FIGS. 7A and 7B are discussed below concurrently.

Pin 612 can include tapered portion 612*t*, groove 617, and proximal portion 650. Lock 700 can include body 702, biasing element 704, projection 706, and face 708. Also shown in FIG. 7A is biasing element 614, pin release 616 (which can include stem 646), and stopper 625. Also shown in FIGS. 7A are orientation indicators Proximal, Distal, Upper, and Lower.

Pin 612 can be secured to pin release 616 via stem 646 of pin release 616, where stem 646 can be a protuberance of pin release 616 that connects pin release 616 to pin 612 through slot 522 (of FIG. 5B). Pin release 616 can include thumb ramp 648, which can be a protrusion of pin release 616 extending outward from pin release. Thumb ramp 648 can provide an engagement portion that can provide a user with a surface against which a force can be applied to force pin release 616 proximally (or distally).

FIG. 7A shows pin groove 617, which can be a circumferential groove extending radially into pin 612 and extending around a circumference of pin 612 near proximal portion 650 of pin 612. In some examples, groove 617 can be sized to receive a projection of lock 700 therein, as discussed further below.

Body 702 of lock 700 can be a rigid elongate member engageable with biasing element 704 at a lower portion of body 702. Body 702 can have a geometric shape substantially of a half-cylinder with a full cylinder at base 705 proximate a lower portion of body 702 and with face 708 extending between base 705 and an upper termination of body 702. Projection 706 can extend radially from base 705 and can extend radially outward from face 708. In some examples, projection 706 does not extend beyond the circumference of base 705. In other examples, projection 706 can extend more or less along face 708, more or less radially outward, and can include more than one projection.

In some examples, projection 706 can be sized to extend fully into lock groove 617 of pin 612 when an outer surface of pin 612 engages face 708 of lock 700. In some examples, projection 706 can be sized to engage about a quarter of a circumference of groove 617 so that lock 700 only has to be displaced toward biasing element 704 a relatively short distance to free pin 612 from lock 700. Also, an outer surface of projection 706 can have a curvature substantially complementary to a curvature of lock groove 617 to help maximize overlap between projection 706 and lock groove 617.

Also shown in FIG. 7B is biasing element 704, which can engage a lower portion of base 705 to bias lock 700 to extend from lock bore 635 of body 602 of end effector coupler 600, as shown in FIG. 6.

Figure 8:
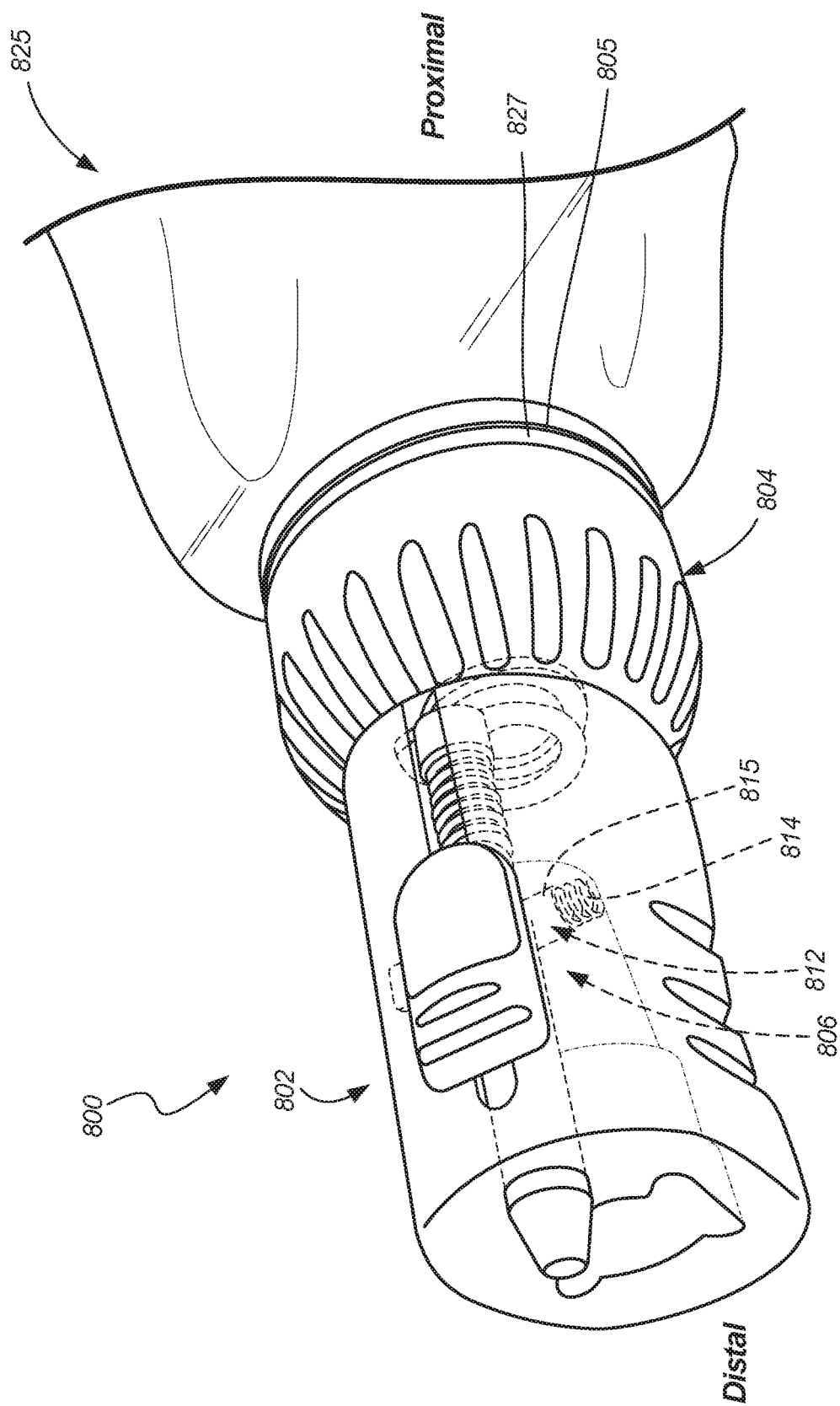
FIG. 8 illustrates a perspective view of an end effector coupler, in accordance with at least one example of this disclosure.

FIG. 8 illustrates a perspective view of end effector coupler 800, in accordance with at least one example of this disclosure. In this example, the end effector coupler is illustrated including a sterile drape for protecting the surgical arm, such as surgical arm 200. Any of the previously discussed end effectors can include similar structures to support application of a sterile drape.

End effector coupler 800 can include body 802, proximal coupler 804, and lock 806. Proximal coupler 804 can include groove 805. Lock 806 can include body 812, base 815, and biasing element 814. Also shown in FIG. 8 is drape 825, which can include O-ring 827. Also shown in FIG. 8 are orientation indicators Proximal and Distal.

End effector coupler 800 can be similar to end effector couplers 500 and 600 described above, except that proximal coupler 804 can include groove 805, which can be a circumferential groove extending around a periphery of proximal coupler 804 near a proximal end of proximal coupler 804. Groove 805 can have a depth and width sized to receive and retain O-ring 827 of drape 825, as discussed below.

Drape 825 can be a protective covering comprised of light weight and non-porous materials such as plastics and the like. In some examples, drape 825 can be disposable, and in other examples, drape 825 can be reusable. Drape 825 can include O-ring 827 at a distal termination of drape 825. O-ring 825 can be sized and shaped to be inserted into groove 805 of proximal coupler 804. Insertion of O-ring 826 into groove 805 allows drape 825 to cover all of a surgical arm except for end effector coupler 800. However, because end effector 800 can be cleanable (autoclavable) as can tools connecting thereto, by covering the surgical arm (which may not be autoclavable) each component of a surgical system using end effector coupler 800 can be reusable, which can help to save cost.

FIG. 8 also shows how body 812 of lock 806 can be disposed within body 802 and how biasing element 814 can engage base 815 to bias lock 806 to extend from body 802.

Figure 9A:
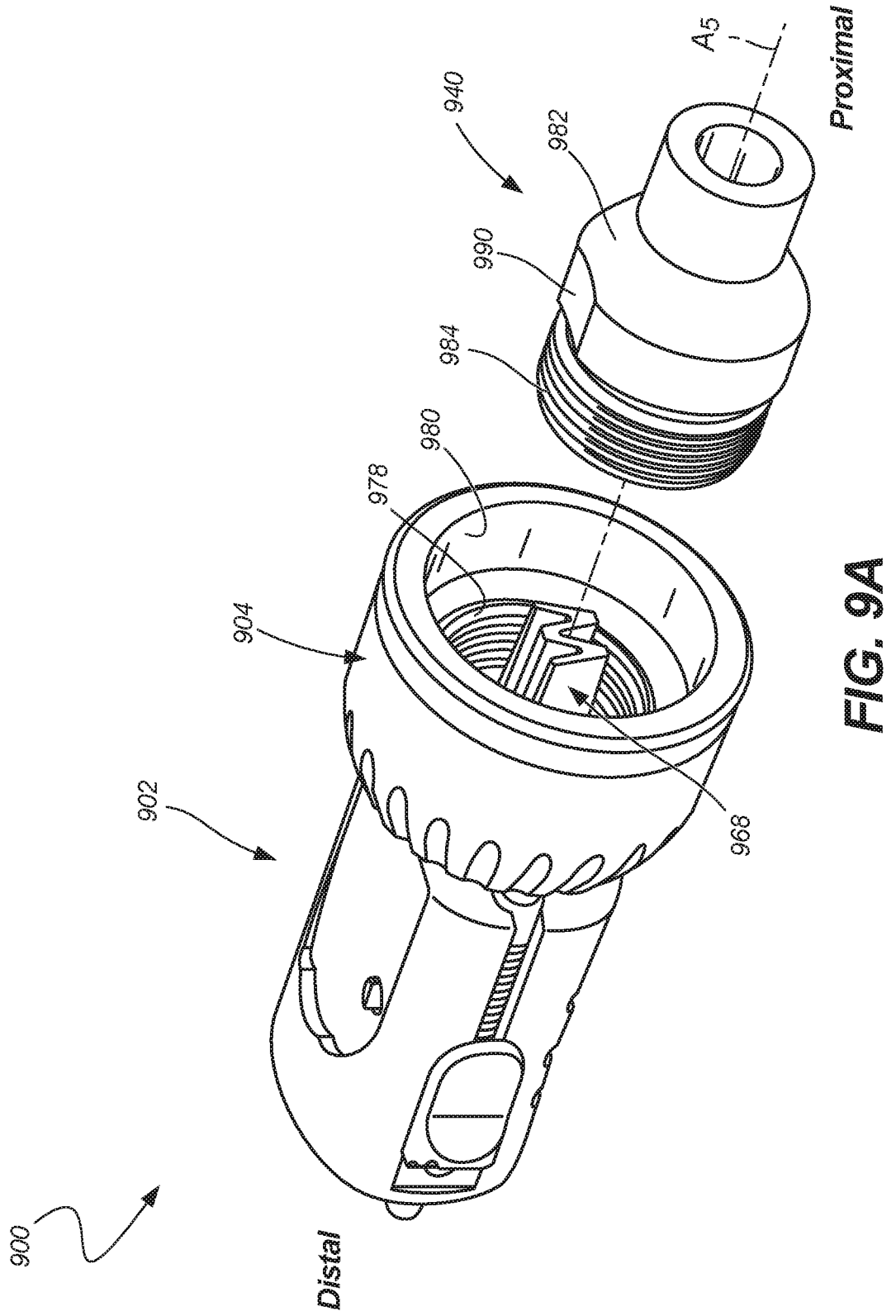
FIG. 9A illustrates a perspective view of an end effector coupler, in accordance with at least one example of this disclosure.
Figure 9C:
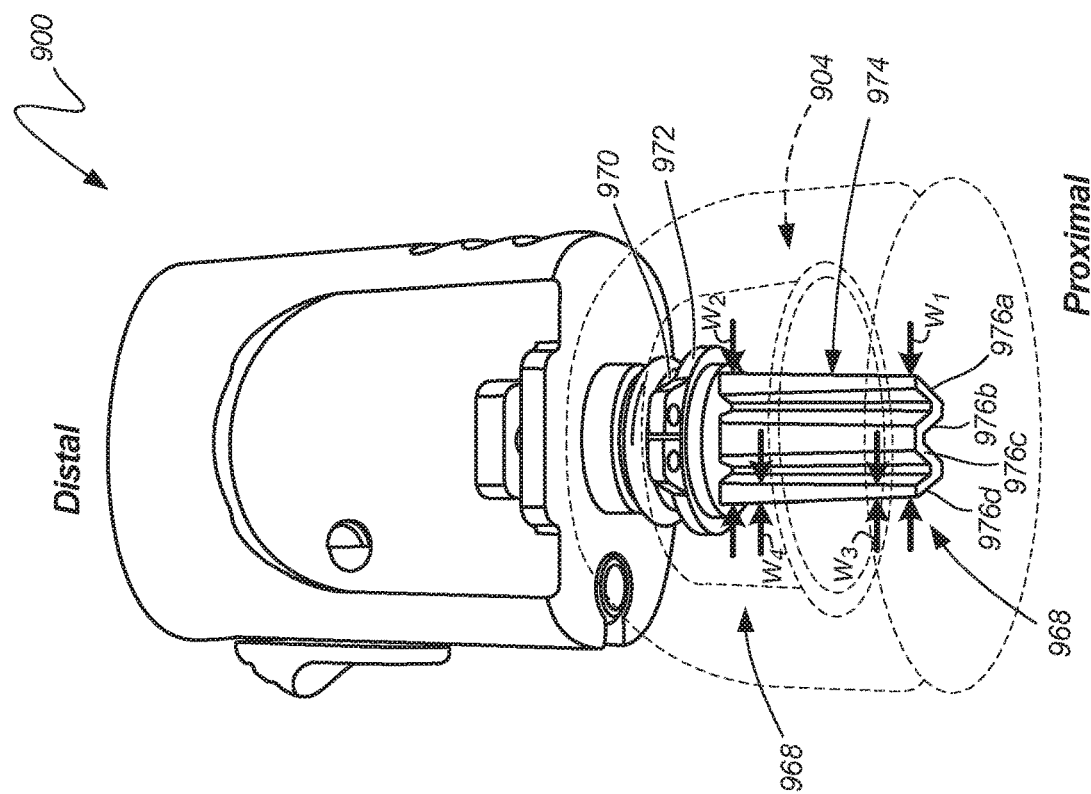
FIG. 9C illustrates a perspective view of an end effector coupler, in accordance with at least one example of this disclosure.

FIG. 9A illustrates a perspective view of end effector coupler 900, in accordance with at least one example of this disclosure. FIG. 9B illustrates a perspective view of an end effector coupler 900, in accordance with at least one example of this disclosure. FIG. 9C illustrates a perspective view of an end effector coupler 900, in accordance with at least one example of this disclosure. FIGS. 9A, 9B, and 9C are discussed below concurrently. The end effector coupler illustrates a protrusion including a taper having a w-shape configured for insertion into a distal connector having a w-shape bore. The w-shape taper-to-taper interface can help limit relative movement of the end effector coupler, can help to quickly orient the end effector coupler relative to the surgical arm, and can help prevent improper end effector couplers from being secured to the surgical arm. Any of the previously discussed end effectors can include similar structures to support a w-shaped taper-to-taper interface.

End effector coupler 900 can include body 902, proximal coupler 904, distal connector 940 of a surgical arm, and ring 972 (shown in FIG. 9C). Body 902 can include protrusion 968. Proximal coupler 904 can include threaded portion 978, and counter bore 980. Protrusion 968 can include collar 969 (which can include grooves 970 and 971), and taper 974 (including segments 976*a*, 976*b*, 976*c*, and 976*d*). Distal connector 940 can include flange 982, threaded insert 984, protrusion tapered bore 986 (which can include slots 986*a*, 986*a*, 986*b*, 986*c*, and 986*d*), and face 988. Also shown in FIG. 9A is axis A5. Also shown in FIG. 9B are heights h1, h2, and h3. Also shown in FIG. 9C are widths w1, w2, w3, and w4. Also shown in FIGS. 9A-9C are orientation indicators Proximal and Distal.

FIG. 9A shows body 902 coupled to collar 904 and separated from distal connector 940, where all three components are substantially in axial alignment about axis A5. FIG. 9B shows collar 904 removed from protrusion 968 and FIG. 9C shows collar 904 in phantom and does not show distal connector 940. Body 902 can be consistent with body 502, for example, but FIGS. 9A and 9B show protrusion 968 extending proximally from a proximal portion of body 902.

Protrusion 968 includes grooves 970 and 971, which can be circumferential grooves around protrusion 968 between body 902 and taper 974. Groove 971 can be sized to retain collar 904 and groove 970 can be sized to retain ring 972 (which can retain collar 904). Ring 972 can be a retaining ring, such as a snap ring or retainer, in some examples, where ring 972 can be sized to be disposed in groove 970 and can be selected to retain or captivate collar 904 on protrusion 968.

Taper 974 can be a tapered portion of protrusion 968 and can have multiple tapered portions of varying taper sizes and/or styles including Brown, Morse, Jarno, Jacobs, and the like tapers. In the examples shown in FIGS. 9A-9C, taper 974 can be a taper having a substantially W-shape from a proximal perspective, where taper 974 becomes smaller as it extends proximally.

As shown in FIG. 9B, segment 976d (along with segments 976a-976c) can have a height of h1 at a proximal end of taper 974 and a height of h2 at a distal end of taper 974, where height h2 is larger than height h1. Similarly, as shown in FIG. 9C, the width w1 of taper 974 at a proximal end of taper 974 can be smaller than width w2 of a distal end of taper 974. Further, each of segments 976a-976d can have a width that decreases as taper extends proximally. For example, width w3 of segment 976d at a proximal end of taper 974 can be smaller than width w4 of segment 976d at a distal end of taper 974.

Taper 974 can be shaped complementary to protrusion tapered bore 986 to provide a taper-to-taper connection between end effector coupler 900 and distal connector 940 (and therefore between end effector coupler 900 and a surgical arm), helping to prevent unwanted movement of end effector coupler 900 and the surgical arm.

More specifically, each of slots 986a, 986b, 986c, and 986d can be shaped complimentary to each of segments 976a, 976b, 976c, and 976d, respectively, so that each of segments 976a-976d is received in a corresponding tapered slot 986a-986d. Accordingly, a distal portion (near face 988) of each of each of slots 986a, 986b, 986c, and 986d can have a larger height and width than a proximal portion of each of slots 986a, 986b, 986c, and 986d, respectively. The w-shape of taper 974 and protrusion tapered bore 986 can be symmetric about one plane, but asymmetric about transverse second and third planes. This asymmetry can be used to quickly align taper 974 relative to protrusion tapered bore 986 to quickly orient end effector coupler 900 relative to distal connector 940 and the surgical arm during attachment of end effector coupler 900.

When disposed within respective slots 986a, 986b, 986c, and 986d, respectively, each of segments 976a, 976b, 976c, and 976d can prevent rotation of end effector coupler 900 relative to distal connector 940 and the surgical arm during attachment or movement of end effector coupler 900. Though a W-shape of taper 974 is shown in FIGS. 9A-9C, other shapes, other shapes can be used, such as a Z-shape, a T-shape, a B-shape, and the like. Also, the W-shape of taper 974 can be the same as an M-shape rotated 180 degrees.

Proximal coupler 904 can include threaded portion 978, which can be a female threaded portion configured to receive threaded insert 984 of distal connector 940. Counter bore 980 of proximal coupler 904 can be sized and shaped to receive and retain flange 982 of distal connector 940 therein, in some examples, where flange 982 is a radial extension from distal connector 940 positioned at a proximal termination of threaded insert 984. Threaded insert 984 can be a male threaded portion configured to threadably engage female threading of threaded portion 978, in some examples In assembly of some examples, collar 904 can be placed on protrusion 968 in groove 971 proximate body 902. Ring 972 can then be secured to protrusion in groove 970 to retain collar 904 between ring 972 and body 902 such that collar 904 is secured to body 902, as shown in FIG. 9B. However, ring 972 does not firmly engage coupler 904 against body 902, allowing proximal coupler 904 to spin or rotate independent of body 902.

Then, as shown in FIG. 9C, taper 974 can be inserted into protrusion tapered bore 986 of distal connector 940 and threaded insert 984 can be inserted into threaded portion 978 of proximal coupler 904. Proximal coupler 904 can then be rotated to threadably secure threaded insert 984 to threaded portion 978, drawing taper 974 completely into tapered bore 986, thereby securing body 902 to distal connector 940. During threading of proximal coupler 904 to distal connector 940, proximal coupler contacts a distal side of ring 972 to draw body 902 proximally toward distal connector 940. Following a procedure, this process can be reversed to remove end effector coupler 902 for cleaning (autoclaving) helping to make end effector coupler 900 reusable.

FIG. 9A also shows flat 990 of flange 982 which can be used to couple to a tool, such as a wrench for retaining distal connector 940 during connection of distal connector 940 to end effector coupler 9000.

Figure 9D:
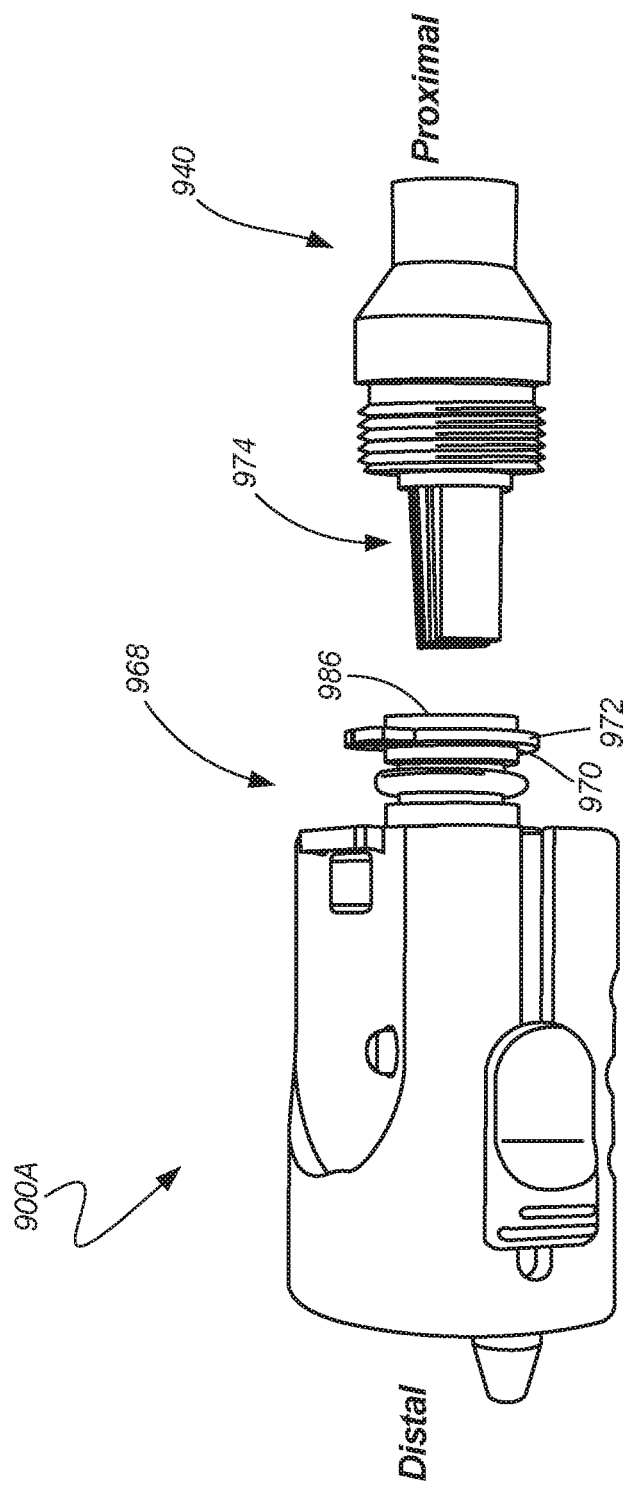
FIG. 9D illustrates a perspective view of an end effector coupler, in accordance with at least one example of this disclosure.

FIG. 9D illustrates a perspective view of end effector coupler 900A, in accordance with at least one example of this disclosure. End effector coupler 900A can be similar to end effector coupler 900 discussed above except that protrusion 968 can include bore 986 and distal connector 940 can include taper 974.

In this example, taper 974 of distal connector 940 of end effector coupler 900A can be similar to taper 968 of end effector coupler 900 of end effector coupler 900, except that taper 974 extends distally from distal connector 940 instead.

Figure 10:
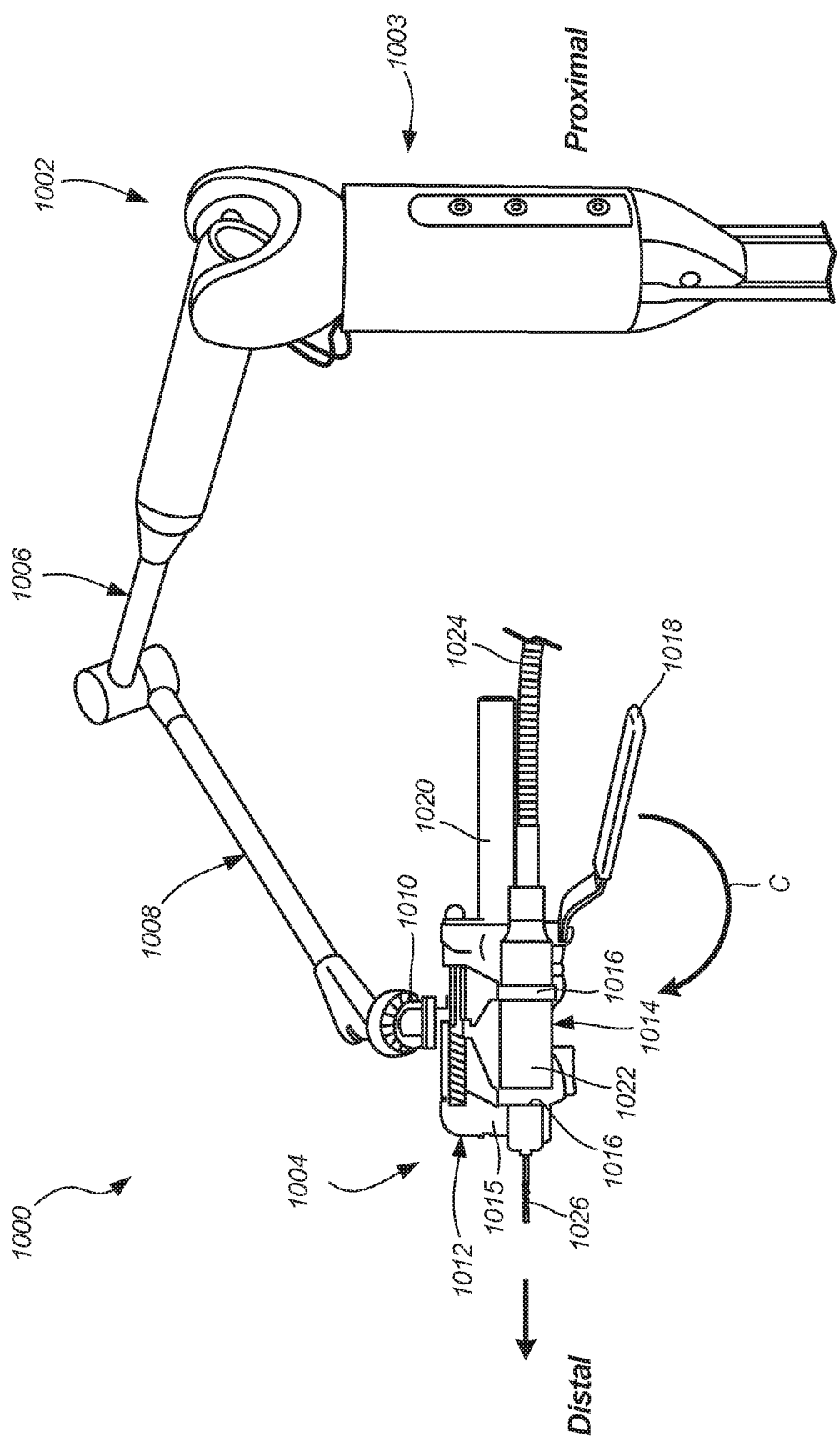
FIG. 10 illustrates a perspective view of a surgical system, in accordance with at least one example of this disclosure.

FIG. 10 illustrates a perspective view of surgical system 1000, in accordance with at least one example of this disclosure. Surgical system 1000 can include surgical arm 1002 and drill tool 1004. Surgical arm 1002 can include control device 1003, arms 1006 and 1008, and end effector coupler 1010. Surgical arm 1002 can be consistent with surgical arm 204 discussed above with respect to FIGS. 2A and 2B, but can be adapted to receive a drill tool configured to turn the surgical arm into a positionable drill press. Any of the previously discussed surgical arms can include similar structures to support a drill tool or drill press.

Drill tool 1004 can include drill support 1012 and drill 1014. Drill support 1012 can include base 1015, clamps 1016, handle 1018, and guide rail 1020. Drill 1014 can include driver 1022, cord 1024, and bit 1026. Also shown in FIG. 10 are arc C and orientation indicators Proximal and Distal.

Drill support 1012 can be a rigid body including a stationary portion coupleable to end effector coupler 1010 and a translatable portion (base 1015) disposed on guide rail 1020 (which can be coupled to the stationary portion). Base 1015 can be a rigid base or support configured to partially engage and support drill 1014 and to secure drill 1014 to end effector coupler 1010.

End effector coupler 1010 can be similar to end effector couplers 500, 600, and 800 described above. Drill support 1012 of drill tool 1004 can include a tool stem (similar to stem 525 of FIGS. 5A and 5B), where the stem can be configured to secure drill tool 1004 to end effector coupler 1010.

Clamps 1016 can extend from base 1015 and can wrap around driver 1022 to secure driver 1022 of drill 1014 to support 1012. In some examples, clamps 1016 can releasably secure drill 1014. Handle 1018 can be a rotatable handle pivotably coupleable to base 1015 and/or a portion of guide rail 1020. Handle 1018 can be an operable actuator configured to move base 1015 and drill 1014 along guide rail 1020 (such that guide rail 1020 can guide translation of support 1012).

Drill 1014 can be an electric drill configured to rotate driver 1022 at a relatively high speed for drilling and cutting operations using bit 1026. Bit 1026 can be a drill bit and can be either fixed or removably coupled to a distal portion of driver 1022 (such as through a chuck). Cord 1024 can be an electrical cord connected to proximal end of driver 1022 and can supply power to and communication information data to and from driver 1012.

In operation of some examples, support 1012 can be secured to end effector coupler 1010 to secure drill tool 1004 to surgical arm 1002. Surgical arm 1002 can then be positioned to place drill bit 1026 in a desired position relative to, for example, a bone. Drill 1014 can then be powered on using control device 1003 or a separate controller or switch coupled to drill 1014. While drill 1014 is powered on, driver 1022 can cause rotation of bit 1026. When bit 1026 is at a desired rotational speed, handle 1018 can be actuated along arc C to translate bit 1026 distally. When a drilling operation is complete, handle 1018 can be rotated in a direction opposite arc C to translate drill 1014 (and therefore bit 1026) along guide rail 1020.

In some examples, surgical arm 1002 can then be repositioned for an additional drilling procedure. In this way, surgical arm 1002 can be an effective drill press with the addition of drill tool 1004 to help provide users the ability to effectively drill straight bores during operations.

FIG. 11A illustrates a perspective view of drill system 1100 in a first condition, in accordance with at least one example of this disclosure. FIG. 11B illustrates a perspective view of drill system 1100 in a second condition, in accordance with at least one example of this disclosure.

Drill system 1100 can include end effector coupler 1102, guide 1104, and drill 1106. Guide 1104 can include proximal opening 1108, distal opening 1110, and stem 1112. Drill 1106 can include drill body 1114 and bit 1116. Also shown in FIGS. 11A and 11B are orientation indicators Proximal and Distal. Also shown in FIG. 1B is object 1125 with surface 1127 and diameters D1 (of opening 1008), D2 of drill body 1114, and D3 (of opening 1010).

End effector coupler 1102 can be similar to end effector couplers 500, 600, and 800 described above. Guide 1104 can be a guide tool configured to receive and retain a drill therein. Stem 1112 can be similar to the tool stems discussed above, such as stem 525 of FIG. 5A. Stem 1112 can be configured to be secured to a body of guide 1104 and can be configured to secure guide 1104 to end effector 1102.

Guide 1104 can be rigid or semi-rigid member having a geometric shape substantially of a hollow truncated cone with two open ends. Proximal opening 1108 can be the first open end having a diameter of D1 and distal opening 1110 can be the second open end having a diameter D3, which can be smaller than that of D1 (and D2), in some examples.

Drill 1106 can be similar to drill 1004 discussed above, but drill 1106 can be moved by hand, in some examples (as opposed to translated as a drill press). Drill body 1114 can house an electric motor and drive and can be connected to drill bit 1116, which can extend distally from drill body 1114.

Object 1125 can be a material or object in which it is desired to create a bore or hole, where surface 1127 is an outer surface of object 1125. In some examples, object 1125 and surface 1127 can be an outer surface of cortical or compact bone.

In operation of some examples, drill guide 1104 can be coupled to end effector 1112 to secure drill guide 1104 to a surgical arm (as discussed above with respect to other tools). End effector coupler 1102 and the surgical arm can then be used to position guide 1104 as desired near object 1125, as shown in FIG. 10B. Drill 1106 can then be inserted through proximal opening 1108 into guide 1104. Because diameter D1 can be sized to be larger than diameter D2 of body 1114 of drill 1104, drill 1106 can be inserted into guide 1104. However, because distal opening 1110 has a diameter D3 smaller than D2 of body 1014, insertion of body 1114 into guide 1104 can be limited by contact between a distal portion of body 1114 and an internal surface of guide 1104 between openings 1108 and 1110. In some examples, the position where contact occurs between a distal portion of body 1114 and an internal surface of guide 1104 can be selected for a desired extension of bit 1116 beyond distal opening 1110. Drill 1106 can be turned on so that bit 1116 is rotating either before or after insertion of drill 1106 into guide 1104.

In some examples, drilling of a bore into object 1125 can be performed as drill 1106 is inserted into guide 1104. In other examples, drilling of a bore into object 1125 can be performed using the surgical arm after drill 1106 is inserted into guide 1104.

In other examples, guide 1104 can have a shape substantially of a cylinder with a small opening at a proximal end so that guide 1104 can be used to guide drill 1106 to create a substantially straight bore as drill 1106 is inserted into guide 1104. Similarly, in some examples, D3 can be only marginally smaller than D1 to guide creation of a bore in object 1125 using bit 1126 by inserting drill 1106 into guide 1104.

In some examples, operation of drill 1106 of FIG. 11 and/or drill 1014 of FIG. 10 can be controlled by a controller, such as controller 402 of FIG. 4. The controller can be used to control the drill, such as controlling whether the drill is on and off and controlling a speed of the drill bit.

Figure 12:
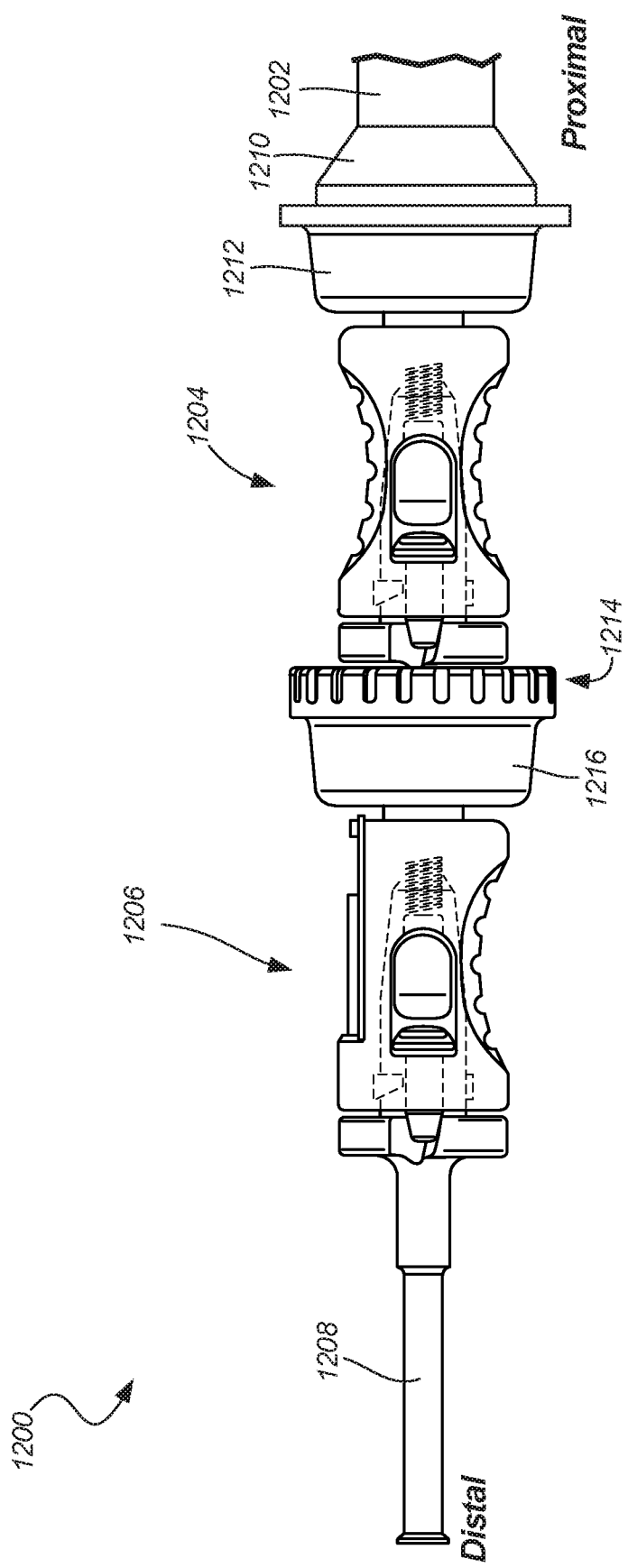
FIG. 12 illustrates a perspective view of an end effector coupler and surgical arm coupler, in accordance with at least one example of this disclosure.

FIG. 12 illustrates a perspective view of end effector coupler 1206 and surgical arm coupler 1204, in accordance with at least one example of this disclosure. The surgical arm coupler can be secured to (or integral to) a surgical arm for receiving a releasably securable end effector coupler. Any of the previously discussed end effectors can include similar structures to support coupling to a surgical arm coupler Coupler system 1200 can include surgical arm 1202, arm coupler 1204, end effector coupler 1206, and stem 1208. Surgical arm 1202 can include distal coupler 1210. Arm coupler 1204 can include proximal coupler 1212. End effector coupler 1206 can include stem coupler 1214 (including collar 1216).

Surgical arm 1202 can be similar to those discussed above, such as arms 104 and 204. Distal coupler 1210 can be rigidly secured to proximal coupler 1212 through, for example welding, such that arm coupler 1204 is not removable from surgical arm 1202. Arm coupler 1204 can be similar to end effector couplers discussed above (such as end effector coupler 500) in that arm coupler 1204 can receive stem therein. For example, arm coupler can receive stem coupler 1214 of end effector coupler 1206.

In some examples, stem coupler 1214 can be a stem secured to a distal portion of end effector coupler 1206 and can include a stem having a profile similar to those discussed above (such as stem 526 of FIG. 5A). Stem coupler 1214 can be insertable into arm coupler 1204 to releasably secure end effector coupler 1206 to arm coupler 1204. Then, a tool (including stem 1208) can be coupled to end effector coupler 1206 using stem 1208 in a similar manner to the coupling of stem 525 to end effector coupler 500 described above.

Coupler system 1200 can thereby provide a way to releasably secure tools to surgical arm 1202 using end effector coupler 1206 in a way that end effector coupler 1206 is also removable so that the tool and end effector coupler 1206 can be cleanable. These components can also help to ensure that improper tools are not secured to arm 1202. In some examples, collar 1216 can receive and retain a drape (similar to end effector coupler 800 of FIG. 8) so that arm coupler 1204 can be kept sanitary during operations. Also, in some examples, collar 1216 may not be rotatable relative to the remainder of end effector coupler 1206, but can rigidly secured thereto so that rotation of end effector coupler 1206 causes rotation of the stem securable to arm coupler 1204.

FIG. 13A illustrates a perspective view of end effector coupler 1300, in accordance with at least one example of this disclosure. FIG. 13A illustrates a perspective view of end effector coupler 1300, in accordance with at least one example of this disclosure. FIGS. 13A and 13B are discussed below concurrently.

End effector coupler 1300 can include body 1302, proximal coupler 1304, stem 1308, and button 1310. Button 1310 can include component 1312 and coupler 1304 can include component 1314. Also shown in FIG. 13A is arm 1306 and orientation indicators Proximal and Distal.

End effector coupler 1300 and the components thereof can be similar to the end effector couplers discussed above, such as end effector couplers 500, 600, and 800. However button 1310 can differ in that it includes component 1312 and proximal coupler 1304 can differ in that it includes component 1314. In FIG. 13A, each of components 1312 and 1314 can be a component (such as a transceiver, transmitter, or receiver) configured to communicate using wireless (electromagnetic) signals through protocols such as WiFi, Bluetooth (Bluetooth LE), Near-Field Communications (NFC), and the like.

In operation of some examples, component 1312 can be part of a electronic circuit that includes button 1310 where button 1310 cannot send or receive signals unless component 1312 is electrically coupled to component 1314. In some examples, relay logic can be used and component 1312 can be a wireless switch preventing button 1310 from completing a circuit. In other examples, component 1312 can be a transceiver in communication with a controller, where the controller will prevent communication between button 1310 and other components unless component 1312 is in communication to component 1314.

In some examples, a specified proximity between components 1312 may be required to operate button 1310 to ensure that button 1310 is coupled to body 1302. For example, a strength of signal indicative of a distance between components 1312 and 1314 may be required to be received at component 1312 before button 1310 can communicate with any other components. Additional details of these and other embodiments are discussed below with respect to FIGS. 14A-14F.

In FIG. 13B, components 1312 and 1314 can be other electronic components configured to directly and physically connect to each other so that button 1310 can be operated. In some examples, as discussed further below, component 1314 can be a passive electrical component, such as a resistor, inductor, and the like, and component 1312 can be an active circuit. For example, component 1314 can be a resistor having a particular resistance to modify a signal (voltage and/or current) generated by 1312. Component 1312 can receive the modified signal and can unlock button 1310 only when the signal is detected as being modified by a predetermined resistance. This can help prevent improper components from being used with surgical arm 1306.

Figure 14A:
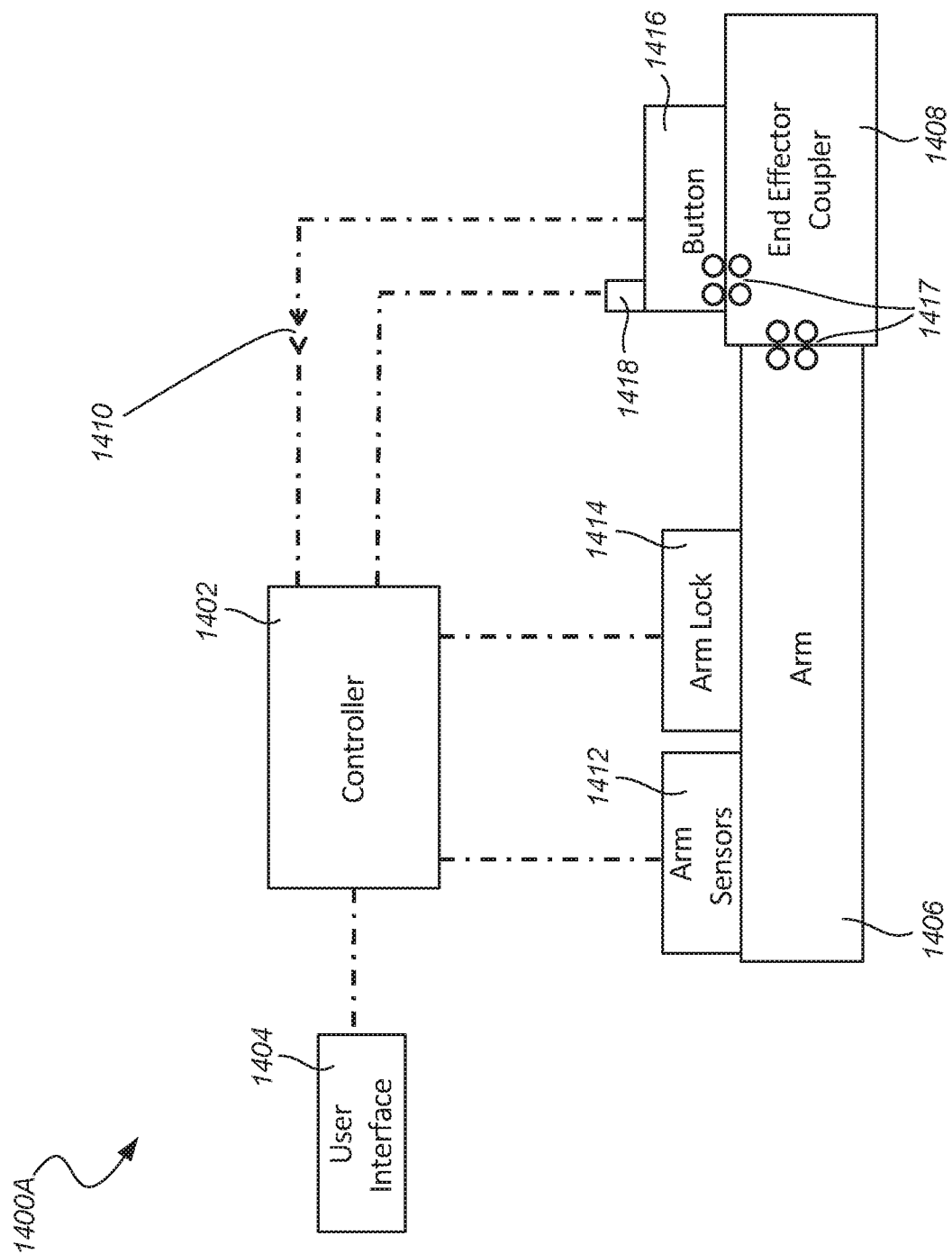
FIG. 14A illustrates a schematic view of a surgical system, in accordance with at least one example of this disclosure.

FIG. 14A illustrates a schematic view of surgical system 1400A, in accordance with at least one example of this disclosure. Surgical system 1400A can include controller 1402, user interface 1404, arm 1406, end effector coupler 1408, connector 1410, arm sensors 1412, arm lock 1414, button 1416, and terminals 1417. Button 1416 can include component 1418. Though button 1416 is shown as being a separate component from end effector coupler 1408, button 1416 can be integral to end effector coupler 1408 (or arm 1406 in other examples).

Controller 1402 can be a programmable controller, such as a single or multi-board computer, a DDC, or a PLC. In other examples controller 402 can be any computing device, such as a handheld computer, for example, a smart phone, a tablet, a laptop, a desktop computer, or any other computing device including a processor and wireless communication capabilities.

Control system 1400A can optionally include user interface 1404 that can be in communication with controller 1402. In another example, user interface 1404 can be separate from control system 1400A or can be communicatively coupled to control system 1400A. User interface 1404 can be any display and/or input device. For example, user interface can be a monitor, keyboard, and mouse in one example. In other examples, user interface 1404 can be a touch screen display. In yet another example, user interface 1404 can provide lights, buttons, and/or switches. Controller 1402 and user interface 1404 can include machine readable medium. The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

Surgical arm 1406 can be similar to the arms discussed above with respect to FIGS. 1-13 such that arm 1406 can be a movable arm that is lockable in a desired position. Surgical arm 1406 can be connected to controller 1402 via arm sensors 1412 and arm lock 1414. Arm sensors 1412 can be any sensors incorporated into surgical arm 1406 such as current sensors, temperature sensors, and the like, where arm sensors 1412 are configured to provide operational information about arm 1406 to controller 1402. Arm lock 1414 can be one or more electric, fluid, or gas-powered locks (which can include an actuator, in some examples). Arm lock 1414 can be in communication with controller 1402 and can be operable to translate or otherwise move one or more components (such as an armature) in response to a control signal. Arm lock 1414 can include mechanical or electro-mechanical locks coupled to joints or arms of arm 1406. In other examples, an actuator can be omitted and locks of arm lock 1414 can be individually operable in response to individual or shared control signals from controller 1402.

End effector coupler 1408 can be similar to the end effector couplers discussed above, such as end effector couplers 500, 600, and 800. Connector 1410 can be a connector can be a plug, jack, or other type of connector used to transmit an analog signal. In other examples, connector 1410 can be a digital connector. In some examples, connector 1410 can be used to releasably connect button 1416 to controller 1402.

Lock/unlock button 1416 can be a simple button or switch in some examples and can be in communication with controller 1402. In some examples, button 1416 can be attached to a portion of arm 1406. In other examples, button 1416 can be attached to other components, or can be located on a floor and can be operated as a foot pedal or switch. In other examples, controller 1402 may not be present and lock/unlock button 1416 can be in direct communication with arm lock 1414.

Terminals 1417 can be electrical contacts or connections on end effector coupler 1408, arm 1406, and button 1416. Terminals 1417 can electrically connect button 1416 to end effector coupler 1408 and can connect end effector coupler 1408 to arm 1406. Terminals 1417 can also be connected to wires or conductors disposed within end effector coupler 1408 and arm 1406, which can help reduce a need for external wires or leads to connect button 1416 to controller 1402 and/or arm 1404. In an exemplary embodiment, connecting end effector coupler 1408 to arm 1406 electrically connects terminals 1417 between end effector coupler 1408 and arm 1406. Further, connecting button 1416 to end effector coupler 1408 lines up terminals 1417 between button 1416 and end effector coupler 1408, but such terminals 1417 may not be connected (i.e., a circuit may not be completed) until button 1416 is pressed. Pressing button 1416 may cause terminals between button 1416 and end effector coupler 1408 to touch, thereby send an unlock signal to controller 1402 to initiate power unlocking of arm 1406, and controller 1402 can send a signal to arm lock 1414 to unlock arm 1406, thereby allowing the user to move an instrument and/or arm 1406 to a desired location and orientation relative to a patient. Releasing button 1416 may cause terminals between button 1416 and end effector coupler 1408 to lose contact, thereby sending an unlock signal (or cease sending a lock signal) to controller 1402 to initiate power locking of arm 1406, and controller 1402 can send a signal to arm lock 1414 to lock arm 1406 in the desired position such that joints of arm 1406 cannot articulate and end effector coupler 1408 of arm 1408 cannot move relative to arm 1406.

Component 1418 can be either a passive or active electrical component physically coupled (and in some examples, removably coupled) to button 1416 and in communication with controller 1402 through button 1416 and/or parallel to button 1416. Component 1418 can be configured to determine when button 1416 is coupled to end effector 1408.

In operation of some examples, a user can interact with user interface 1404 to power on control system 1400A. Power can be indicated by a light, for example, on user interface 1404 and/or on arm 1406 and/or button 1416. The user can then operate button 1416 to send an unlock signal to controller 1402 to initiate power unlocking of arm 1406. In response, controller 1402 can send a signal to arm lock 1414 to unlock arm 1406. Once arm 1406 is unlocked, the user can move an instrument and/or arm 1406 to a desired location and orientation relative to a patient.

When the user releases button 1416, button 1416 can send a lock signal (or can cease sending an unlock signal) to controller 1402. In response, controller 1402 can send a signal (or can cease sending an unlock signal) to arm lock 1414, locking arm 1406 in the desired position such that joints of arm 1406 cannot articulate and end effector coupler 1408 of arm 1408 cannot move relative to arm 1406.

In some examples, operation of button 1416 can be prevented by component 1418. In some examples, component 1418 can be can be a passive or active electrical component configured to engage either button 1416 or a portion of end effector coupler 1408 when button 1416 is attached to end effector coupler 1408. Such engagement can allow component 1418 to complete a circuit so that button 1416 can send the unlock signal to controller 1402 to allow arm 1404 to unlock. Or, such engagement can allow component 1418 to transmit the signal to controller 1402 to notify controller 1402 that an unlock signal can be transmitted from controller 1402 to arm lock 1414 when button 1416 is operated. In each case, component 1418 can act as an interlock or safety device, preventing operation of button 1416 until button 1416 is secured to end effector coupler 1408.

Figure 14B:
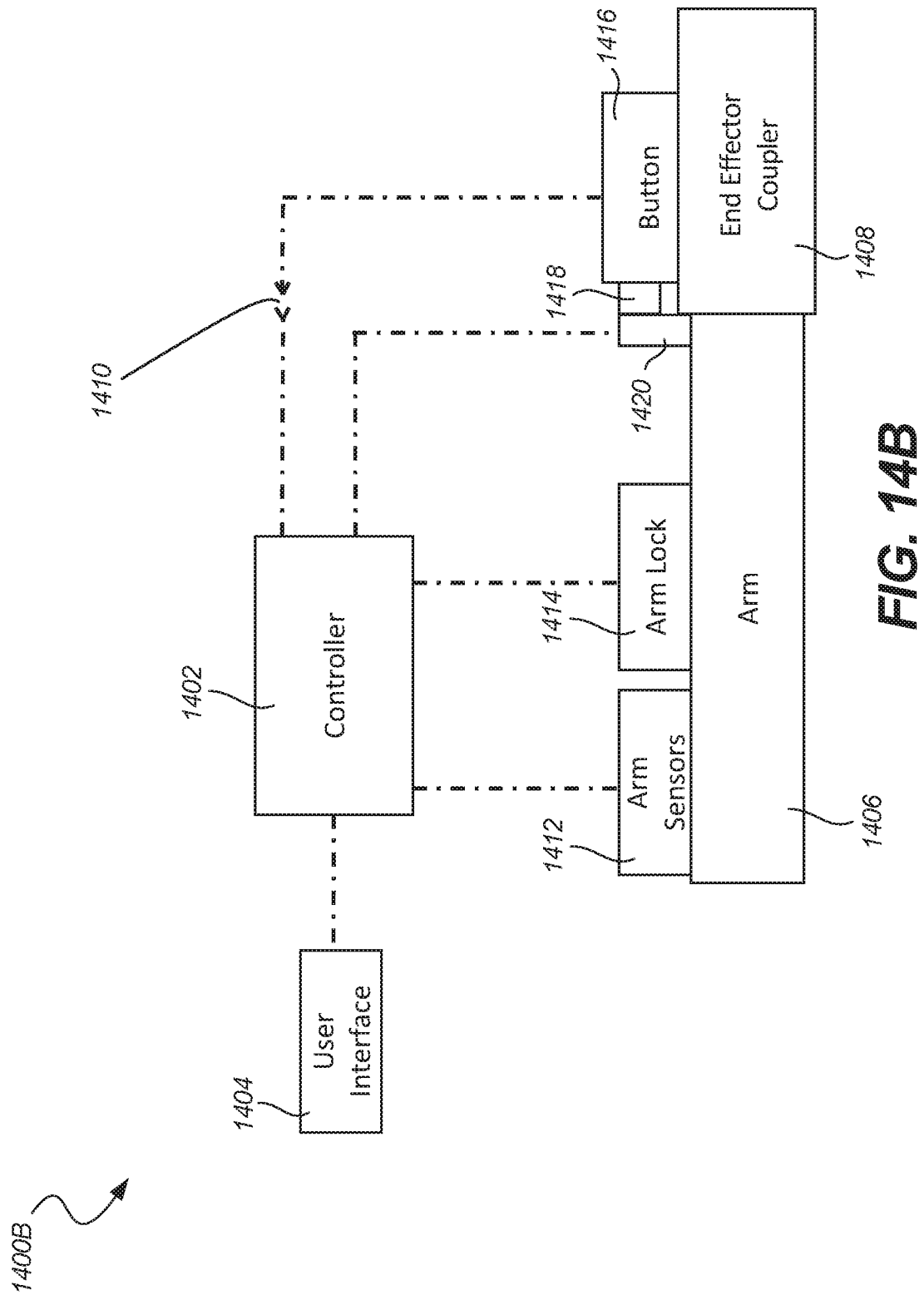
FIG. 14B illustrates a schematic view of a surgical system, in accordance with at least one example of this disclosure.

FIG. 14B illustrates a schematic view of surgical system 1400B, in accordance with at least one example of this disclosure. Surgical system 1400B can be similar to surgical system 1400A, except that surgical system 1400B can include button component 1418 and arm component 1420.

Button component 1418 can be physically connected to button 1416 and arm component 1420 can be physically connected to arm 1406 and/or end effector coupler 1408. In some examples, each of components 1418 and 1420 can be part of an electronic circuit that is electrically coupled to controller 1402. In some examples, component 1418 can be an integral component to button 1416.

In some examples, component 1418 can be a passive electrical component and component 1420 can be an active component or circuit. In either example, the electrical coupling of components 1418 and 1420 (as shown in FIG. 14B) can complete a circuit to transmit an interlock signal to controller 1402 which can notify controller 1402 that arm lock 1414 can be unlocked. In other examples, the electrical coupling of components 1418 and 1420 (as shown in FIG. 14B) can allow a signal to be transferred from component 1418 to component 1420 to notify component 1420 to transfer an interlock signal to controller 1402 indicating that arm lock 1414 can be unlocked.

Figure 14C:
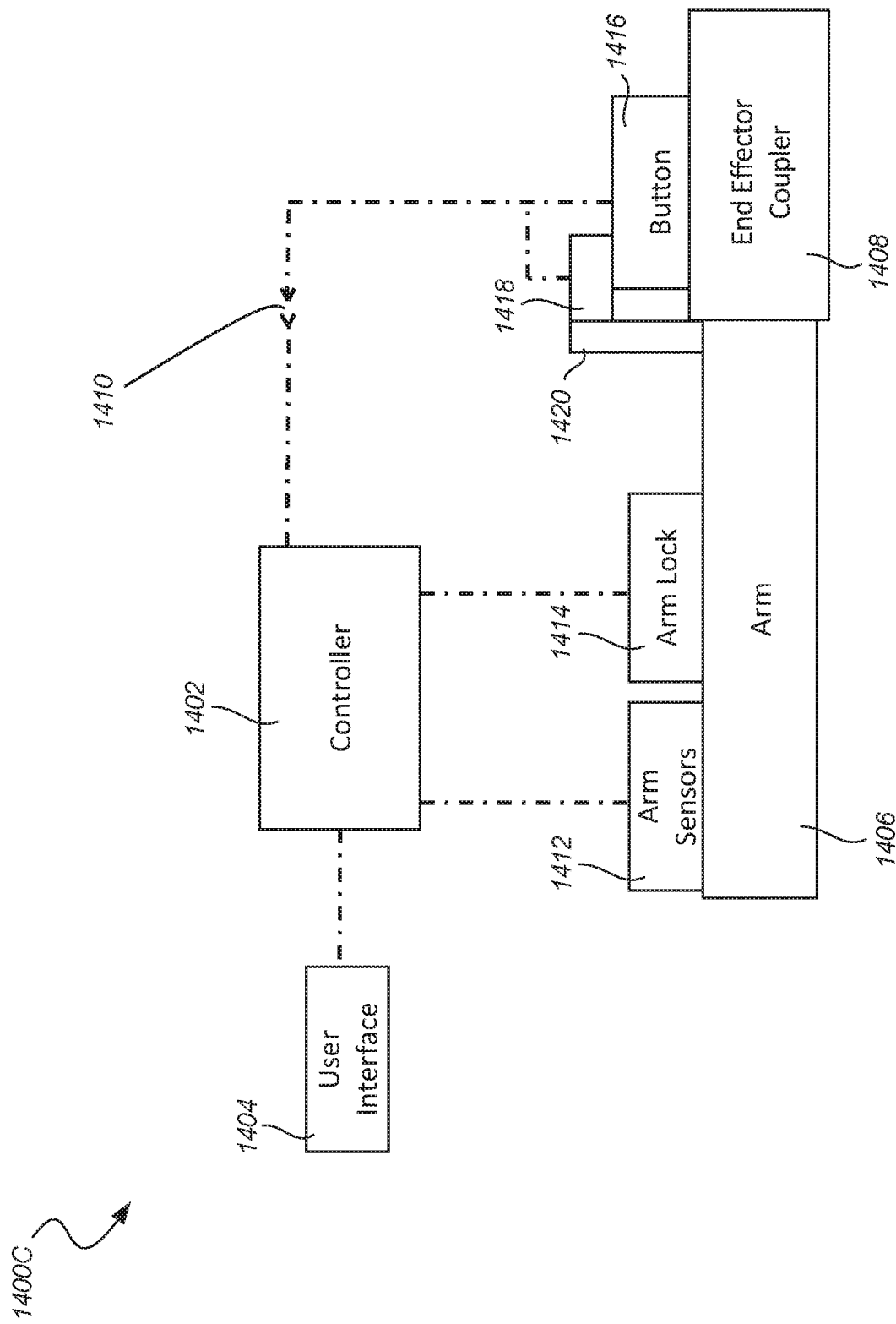
FIG. 14C illustrates a schematic view of a surgical system, in accordance with at least one example of this disclosure.

FIG. 14C illustrates a schematic view of surgical system 1400C, in accordance with at least one example of this disclosure. Surgical system 1400C can be similar to surgical system 1400B, except that component 1418 can be electrically connected to button 1416 or can share a communication circuit connecting button 1416 to controller 1402.

Figure 14D:
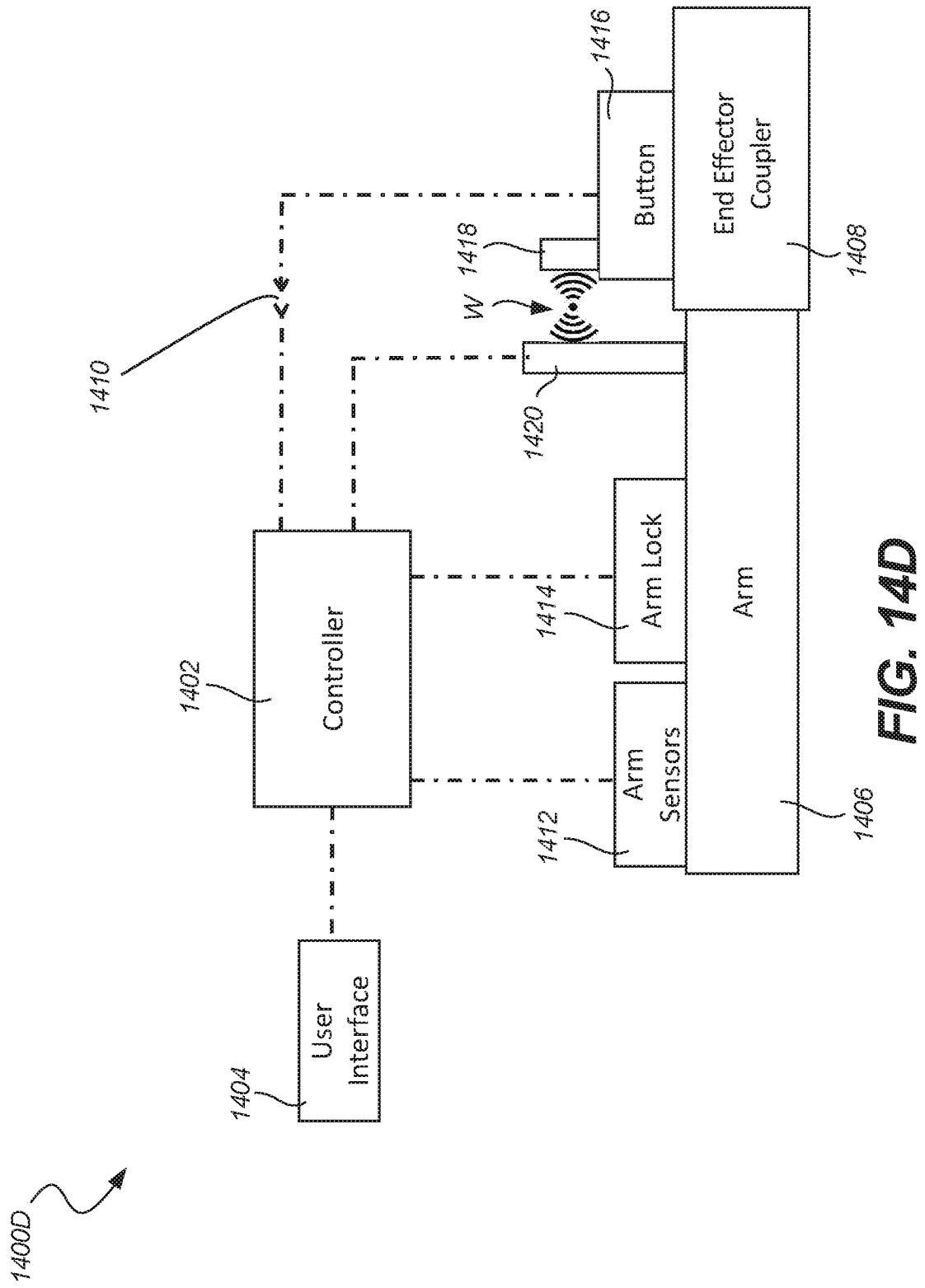
FIG. 14D illustrates a schematic view of a surgical system, in accordance with at least one example of this disclosure.

FIG. 14D illustrates a schematic view of surgical system 1400D, in accordance with at least one example of this disclosure. Surgical system 1400D can be similar to surgical system 1400B, except that each of components 1418 and 1420 can be a component (such as a transceiver) configured to communicate using wireless (electromagnetic) signals (shown as W in FIG. 14D) through protocols such as WiFi, Bluetooth, NFC, and the like. Component 1418 can be physically coupled to button 1416 and component 1420 can be physically coupled to arm 1420. However, in other examples, component 1420 can be physically coupled to other components, such as end effector coupler 1408. Component 1420 can also be electrically coupled to controller 1402.

In operation of some examples, component 1420 can be part of (or can include) an interlock circuit that is connected to controller 1402. The interlock circuit can be configured to transmit a signal to controller 1402 to notify controller 1402 that an unlock signal can be sent to arm lock 1414 when the unlock signal is received from button 1416. The interlock circuit of component 1420 can produce the interlock signal when component 1420 wirelessly couples to component 1418, which indicates that button 1416 is coupled to end effector coupler 1408. In some examples, component 1420 can be configured to send the interlock signal only when a wireless signal of a particular strength is received from component 1408. The signal strength can be selected to indicate that component 1420 is at a distance from component 1418 indicative of button 1416 being coupled to end effector coupler 1408.

Figure 14E:
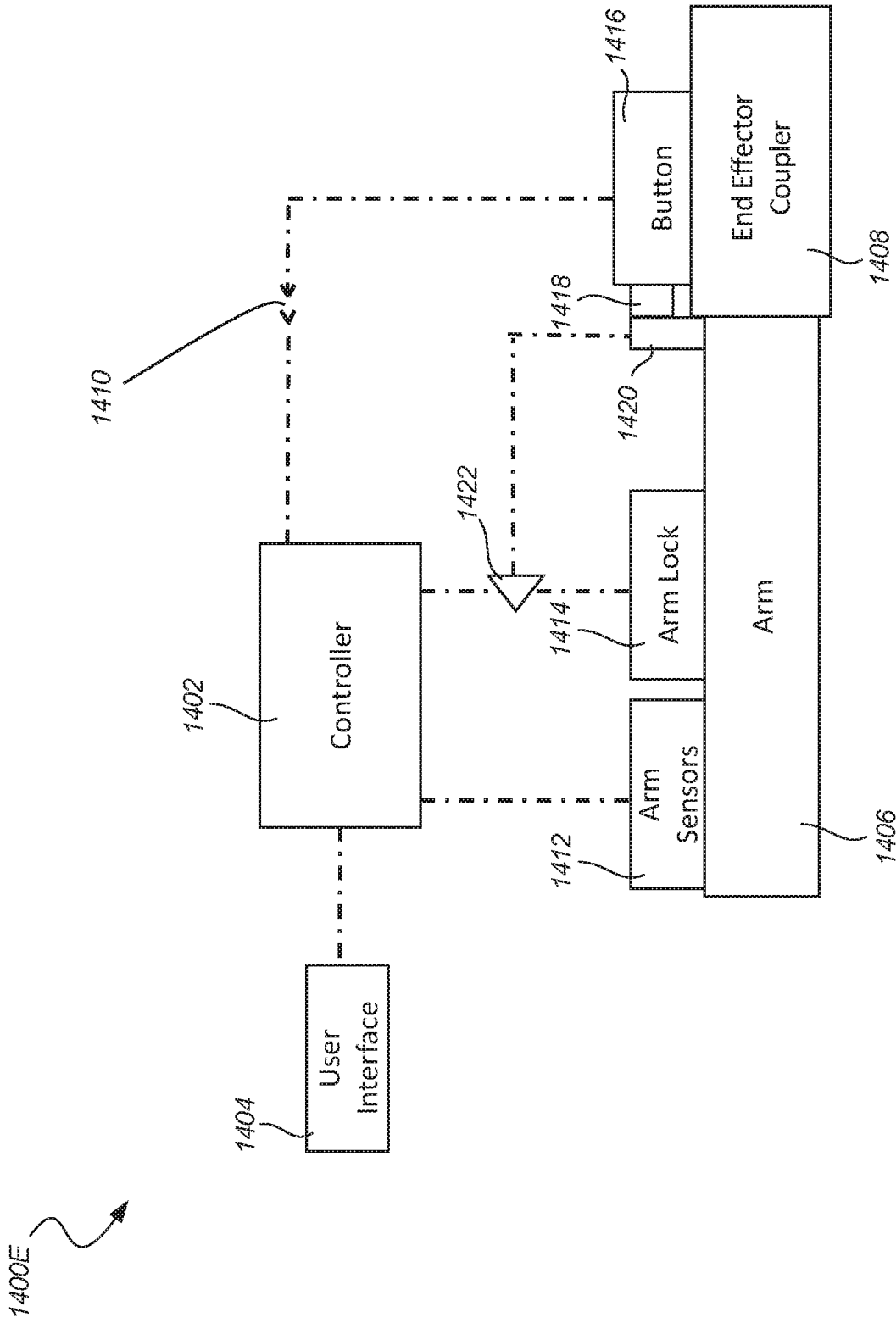
FIG. 14E illustrates a schematic view of a surgical system, in accordance with at least one example of this disclosure.

FIG. 14E illustrates a schematic view of surgical system 1400E, in accordance with at least one example of this disclosure. Surgical system 1400E can be similar to surgical system 1400B, except that component 1420 can be electrically connected to interlock 1422, where interlock 1422 can be electrically connected to controller 1402 and arm lock 1414. Interlock 1422 can be an interlock component including a switch, such as a relay, configured to close to complete the circuit between controller 1402 and arm lock 1414 when interlock 1422 receives a signal from component 1420. In some examples, component 1420 can be configured to produce the interlock signal to be sent to interlock 1422 when component 1420 is electrically coupled to component 1418 (as shown in FIG. 14E) when button 1416 is connected to end effector coupler 1408 and when end effector coupler 1408 is connected to arm 1406. This can help prevent operation of arm 1406 is improper tools without the requirement of an additional input into controller 1420.

Figure 14F:
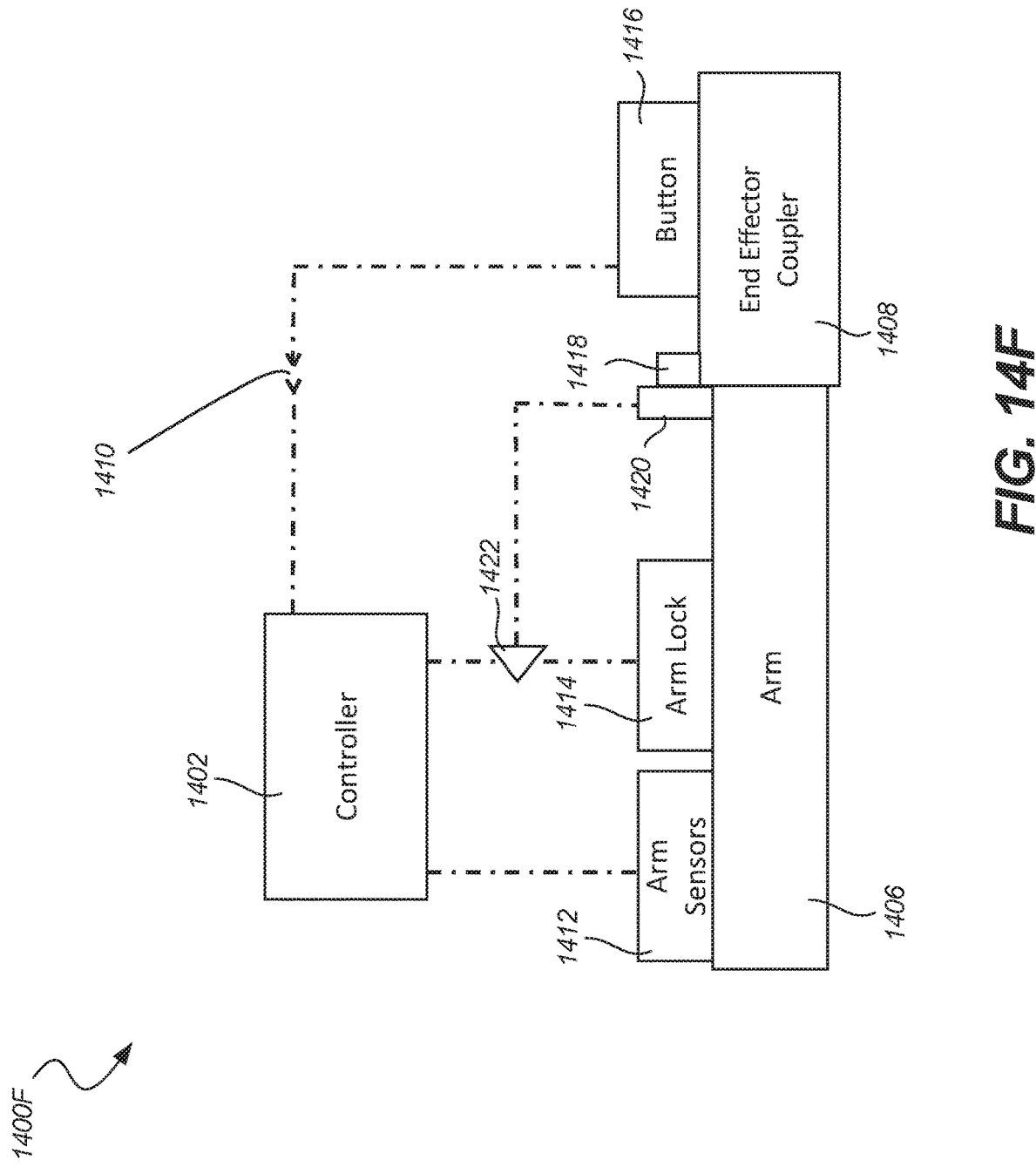
FIG. 14F illustrates a schematic view of a surgical system, in accordance with at least one example of this disclosure.

FIG. 14F illustrates a schematic view of surgical system 1400F, in accordance with at least one example of this disclosure. Surgical system 1400F can be similar to surgical system 1400E, except that component 1418 can be coupled to end effector coupler 1408 to require that end effector coupler 1408 is connected to arm 1406 (and component 1418 is electrically connected to component 1420) before an unlock signal can be sent from controller 1402 to arm lock 1414.

Figure 15:
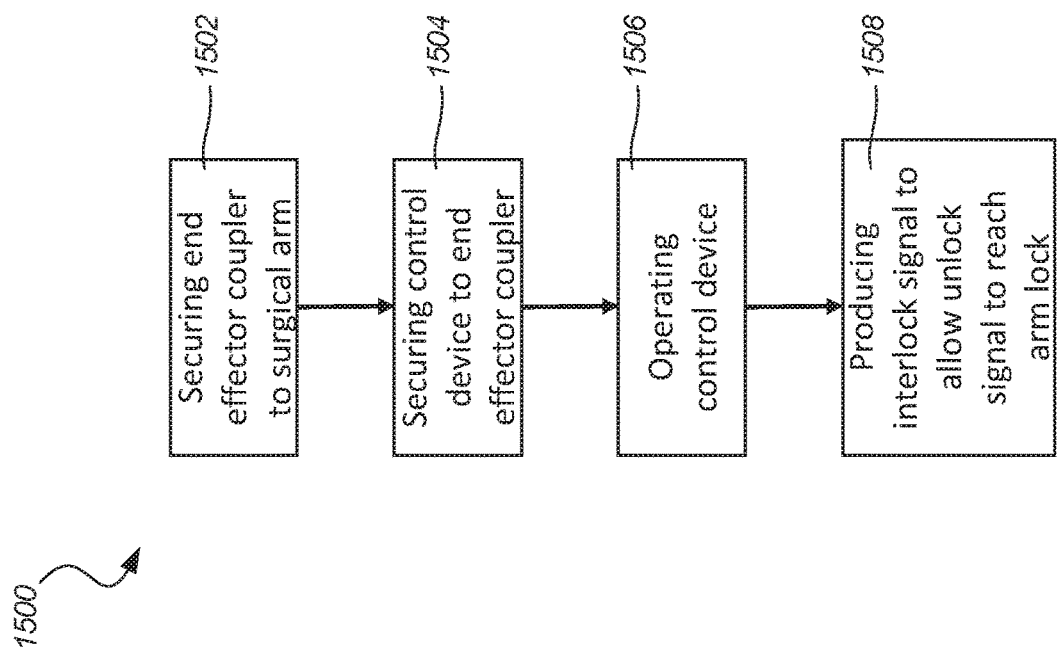
FIG. 15 illustrates a schematic view of a method, in accordance with at least one example of this disclosure.

FIG. 15 illustrates a schematic view of method 1500, in accordance with at least one example of this disclosure. Method 1500 can be a method of connecting an end effector coupler to a surgical arm, unlocking the surgical arm, and using the surgical arm for various surgical procedures. The steps or operations of method 1500 are illustrated in a particular order for convenience and clarity; many of the discussed operations can be performed in a different sequence or in parallel without materially impacting other operations. Method 1500 as discussed includes operations performed by multiple different actors, devices, and/or systems. It is understood that subsets of the operations discussed in method 1500 attributable to a single actor, device, or system could be considered a separate standalone process or method.

The method can begin at step 1502, where an end effector coupler can be secured to a surgical arm. For example, end effector coupler 312 can be secured to surgical arm 308. At step 1504, a control device can be secured to an end effector coupler. For example, button 320 can be secured to end effector coupler 312. Or button 517 can be secured to end effector coupler 500, in another example.

At step 1506, the control device can be operated. For example, button 517 can be depressed to unlock a surgical arm. Or, for example, button 1416 can be operated to send an unlock signal to controller 1402, which can send an unlock signal to arm lock 1414, provided component 1418 and/or 1420 has indicated to controller 1402 that the unlock signal can be sent to arm lock 1414. At step 1508, an interlock signal can be produced to allow an unlock signal to reach an arm lock. For example, component 1418 and/or 1420 can send to controller 1402 an interlock signal, indicating to controller 1402 that the unlock signal can be sent to arm lock 1414. In other examples, as shown in FIG. 14F, the interlock signal can be sent from component 1418 and/or 1420 to interlock 1422 to allow the unlock signal to be transmitted from controller 1402 to arm lock 1414. Though steps 1506 and 1508 are shown in series, these steps can occur in any order and can occur multiple times. Similarly, other steps of method 1500 can be repeated multiple times at any step of method 1500.

EXAMPLES

The following, non-limiting examples, detail certain aspects of the present subject matter to solve the challenges and provide the benefits discussed herein, among others.

Example 1 is a system for a surgical arm, the system comprising: a body comprising a proximal portion and an opposite distal portion, the distal portion including a distal end; a control device couplable to an external surface of the body and operable to transmit a signal to allow movement of the surgical arm.

In Example 2, the subject matter of Example 1 optionally includes wherein the pin limits rotation of the stem relative to the keyed opening to prevent release of the stem from the keyed opening when the pin engages the stem.

In Example 3, the subject matter of any one or more of Examples 1-2 optionally include wherein the body includes a tapered bore aligned along a central axis running through the keyed opening and configured to receive the tool stem therein.

In Example 4, the subject matter of any one or more of Examples 2-3 optionally include wherein the tapered bore is configured to receive a complimentary tapered section of the tool stem to form a taper-to-taper interface to limit relative motion between the end effector coupler and the tool stem.

In Example 5, the subject matter of Example 4 optionally includes wherein the body includes a flat outer surface configured to receive the control device thereon and a tab channel extending through the flat outer surface.

In Example 6, the subject matter of Example 5 optionally includes wherein the control device includes a tab extending from the control device and insertable into the tab channel to releasably secure the control device to the body.

In Example 7, the subject matter of any one or more of Examples 5-6 optionally include a lock extendable through the body and engageable with the pin to restrict translation of the pin relative to the bore.

In Example 8, the subject matter of Example 7 optionally includes wherein the lock extends through the flat outer surface and is displaceable into the body to release from the pin to allow the pin to translate relative to the pin bore.

In Example 9, the subject matter of Example 8 optionally includes wherein the control device is configured to engage the lock to displace the lock into the body when the control device is secured to the body.

In Example 10, the subject matter of any one or more of Examples 7-9 optionally include wherein the pin includes a circumferential groove, and wherein the lock includes a projection engageable with the circumferential groove of the pin to restrict translation of the pin within the pin bore.

In Example 11, the subject matter of Example 10 optionally includes wherein the body includes a lock bore extending into the body substantially transverse to the pin and sized to receive the lock therein.

In Example 12, the subject matter of Example 11 optionally includes a lock biasing element disposed in the lock bore and engaging the lock to bias the lock to a position where the projection engages the circumferential groove of the pin.

Example 13 is an assisted surgical system comprising: a surgical arm positionable in space when the surgical arm is unlocked; an arm lock engageable with the surgical arm to lock the surgical arm in a desired position and to unlock the surgical arm in response to an unlock signal; an end effector coupler comprising: a body comprising a proximal portion and an opposite distal portion, the distal portion including a distal end; a coupler connected to the proximal portion and releasably couplable to the surgical arm; a keyed opening extending through the distal end into the distal portion, the keyed opening configured to secure a tool to the end effector coupler; and a control device couplable to the end effector coupler and operable to transmit the unlock signal to unlock the surgical arm.

In Example 14, the subject matter of Example 13 optionally includes an interlock device configured to produce an interlock signal to allow the unlock signal to be transmitted to the arm lock when the control device is coupled to the end effector coupler.

In Example 15, the subject matter of Example 14 optionally includes wherein the interlock device includes: a stationary component coupled to the surgical arm; and a movable component coupled to the control device, the stationary component connectable to the movable component when the control device is coupled to the end effector coupler to complete an interlock circuit allowing the unlock signal to be transmitted to the arm lock.

In Example 16, the subject matter of any one or more of Examples 14-15 optionally include the interlock device includes: a stationary wireless component coupled to the surgical arm; and a movable wireless component coupled to the end effector coupler such that the stationary wireless component and the movable wireless component can communicate wirelessly when the control device is coupled to the end effector coupler allowing the unlock signal to be transmitted to the arm lock.

In Example 17, the subject matter of any one or more of Examples 14-16 optionally include an arm unlock circuit connected to the arm lock, the arm unlock circuit including an interlock switch, wherein the interlock device connects to the interlock switch to prevent the unlock signal from being delivered to the arm lock to limit movement of the surgical arm until the interlock device transmits an interlock signal to the interlock switch to complete the arm unlock circuit.

In Example 18, the subject matter of any one or more of Examples 13-17 optionally include a tool movable with the surgical arm, the tool including a stem insertable into the keyed opening to secure the tool to the end effector coupler.

In Example 19, the subject matter of Example 18 optionally includes wherein end effector coupler includes: a pin disposed in a pin bore adjacent the keyed opening, the pin extendable from the pin bore to engage and retain the tool stem when the tool stem is inserted into the keyed opening; a biasing element in the pin bore and engaging the pin to bias the pin to extend from the distal end; and a pin release comprising an actuator extending beyond an external surface of the body and engaging the pin, the pin release operable to retract the pin into to the body to disengage the pin from the tool stem allowing release of the tool stem from the keyed opening.

In Example 20, the subject matter of Example 19 optionally includes wherein the stem includes a key bit extending radially from the stem, wherein the keyed opening includes a stem opening and a keyway, the stem opening configured to receive the stem therein, and the keyway extending radially from less than a full circumference of the stem opening, the keyway sized to receive the key bit therethrough to allow the effector to receive the stem.

In Example 21, the subject matter of Example 20 optionally includes wherein the key bit includes an angled face on a distal side of the key bit.

In Example 22, the subject matter of Example 21 optionally includes wherein the keyed opening includes a counterbore extending radially from the keyed opening proximal of the keyway, the counterbore sized to receive the key bit therein to allow the angled face to engage a distal portion of the keyway adjacent the counterbore to limit axial movement of the stem relative to the keyed opening.

In Example 23, the subject matter of Example 22 optionally includes wherein the tool includes a flange extending radially outward from the stem, the flange axially positioned to limit translation of the stem into the end effector coupler.

In Example 24, the subject matter of Example 23 optionally includes wherein the flange includes a notch sized to receive a distal tip of the pin to limit rotation of the tool relative to the end effector coupler when the pin is received within the notch.

In Example 25, the subject matter of Example 24 optionally includes wherein the notch extends through a radially outer portion of the flange and includes an axis not parallel to an axis of the flange to promote contact between the flange and the pin to limit rotation of the tool relative to the end effector coupler when the pin engages the notch.

In Example 26, the subject matter of any one or more of Examples 13-25 optionally include a secondary coupler to secure the end effector coupler to the surgical arm, the secondary coupler comprising: a body comprising a proximal portion secured to the arm and an opposite distal portion, the distal portion including a distal end; a lock for releasably retaining an end effector coupler stem to the end secondary coupler, the lock comprising: a keyed opening extending through the distal end into the distal portion, the keyed opening configured to receive the end effector coupler stem therein; a pin disposed in a pin bore adjacent to the keyed opening, the pin extendable from the pin bore to engage and retain the end effector coupler stem when the end effector coupler stem is inserted into the keyed opening; and a pin release comprising an actuator extending beyond an external surface of the body and engaging the pin, the pin release operable to retract the pin into to the body to disengage the pin from the end effector coupler stem allowing release of the end effector coupler stem from the keyed opening.

Example 27 is a surgical drill press system comprising: a surgical arm positionable in space and operable to lock a position of the surgical arm in a desired position; a stem releasably securable to the surgical arm; a rail secured to the stem, the rail extending along a longitudinal axis; a base supported by the rail to enable the base to linearly translate along the longitudinal axis over a length of the rail; a drill releasably securable onto the base; and an actuator coupled to the base and operable to translate the base and the drill on the rail along the longitudinal axis.

In Example 28, the subject matter of Example 27 optionally includes the drill further comprising: a drill bit coupleable to the drill, the drill operable to rotate the drill bit, the drill bit translatable through operation of the actuator; an electrical connector opposite the drill bit; and a clamp secured to base and adjustable to secure the drill to the base.

In Example 29, the subject matter of any one or more of Examples 27-28 optionally include wherein the handle is rotatable to translate the drill along the rail.

In Example 30, the subject matter of any one or more of Examples 27-29 optionally include the stem further comprising: a key bit extending radially from the stem and including an angled face on a distal side of the key bit; and a flange extending radially outward from the stem proximate the key bit.

Example 31 is a drill system for a surgical arm, the drill system comprising: a surgical arm positionable in space and operable to lock a position of the surgical arm in a desired position; an end effector coupler secured to the surgical arm; a surgical drill operable to create a bore in a bone of a patient; a drill guide sized to receive the drill partially therethrough to guide the drill to a desired location through movement of the surgical arm; and a stem coupled to the drill guide and extending therefrom, the stem releasably securable to the surgical arm.

In Example 32, the subject matter of Example 31 optionally includes wherein the drill guide has a geometric shape of a substantially hollow cone.

In Example 33, the subject matter of any one or more of Examples 31-32 optionally include wherein the drill guide is open at both a proximal end and a distal end of the drill guide.

In Example 34, the subject matter of any one or more of Examples 31-33 optionally include wherein the distal end is sized to allow a bit of the drill to extend therethrough and sized to prevent a body of the drill from extending therethrough.

In Example 35, the subject matter of any one or more of Examples 31-34 optionally include the stem further comprising: a key bit extending radially from the stem and including an angled face on a distal side of the key bit; and a flange extending radially outward from the stem proximate the key bit to limit translation of the stem into the end effector coupler.

Example 36 is an assisted surgical system comprising: a surgical arm positionable in space when the surgical arm is unlocked; an arm lock engageable with the surgical arm to lock the surgical arm in a desired position and to unlock the surgical arm in response to an unlock signal; an end effector coupler comprising: a body comprising a proximal portion and an opposite distal portion, the distal portion including a distal end; a coupler connected to the proximal portion and releasably couplable to the surgical arm; a keyed opening extending through the distal end into the distal portion, the keyed opening configured to secure a tool to the end effector coupler; and a control device couplable to the end effector coupler and operable to produce the unlock signal; and an interlock device configured to produce an interlock signal to allow the unlock signal to be transmitted to the arm lock when one of the control device is coupled to the end effector coupler.

Example 37 is a method of operating an assisted surgical system comprising: securing an end effector coupler to a distal end of a surgical arm; securing a control device to one of the end effector coupler and the surgical arm; operating the control device to produce an unlock signal deliverable to an arm lock to unlock the arm; and producing an interlock signal using an interlock device coupled to one or more of the end effector coupler, the control device, and the surgical arm.

In Example 38, the subject matter of Example 37 optionally includes positioning the arm in space when the arm is unlocked; and operating the control device to stop sending the unlock signal to the arm lock to lock the arm in a selected position.

In Example 39, the subject matter of any one or more of Examples 37-38 optionally include limiting transmission of the unlock signal with an interlock switch coupled to the arm lock when a moveable component located on one of the end effector coupler and the control device is not coupled to a stationary component located on the surgical arm.

In Example 40, the subject matter of any one or more of Examples 37-39 optionally include wherein producing the interlock signal is performed by the interlock device when the control device is coupled to the end effector coupler.

In Example 41, the subject matter of any one or more of Examples 37-40 optionally include securing a tool to the end effector coupler.

In Example 42, the subject matter of any one or more of Examples 37-41 optionally include wherein operating the control device includes pressing button to produce the unlock signal.

Example 43 is a surgical system arm system comprising: a surgical arm positionable in space and operable to lock a position of the surgical arm in a desired position, the surgical arm including a distal coupler coupled to a distal portion of the surgical arm; an end effector coupler configured to receive and retain a tool stem therein, the end effector coupler comprising: an end effector body comprising a proximal portion and an opposite distal portion, the distal portion including a distal end; a proximal coupler connected to the proximal portion and releasably couplable to the surgical arm, the proximal coupler comprising a protrusion having a profile that is substantially W-shaped, the protrusion insertable into the distal coupler to secure the end effector coupler to the surgical arm.

In Example 44, the subject matter of Example 43 optionally includes wherein the distal coupler further comprise a w-shaped bore configured to receive the protrusion therein.

In Example 45, the subject matter of Example 44 optionally includes wherein the w-shaped protrusion is tapered along a central axis running through the protrusion.

In Example 46, the subject matter of Example 45 optionally includes wherein the tapered bore is configured to receive a complimentary tapered section of the tool stem to form a taper-to-taper interface to limit relative motion between the end effector coupler and the tool stem.

In Example 47, the subject matter of Example 46 optionally includes wherein the w-shaped bore of the distal coupler is tapered complimentary to the w-shaped protrusion such that the w-shaped protrusion and the w-shaped bore form a taper-to-taper interface when the w-shaped protrusion is received within the w-shaped bore.

In Example 48, the subject matter of any one or more of Examples 43-47 optionally include a tool lock for releasably retaining a tool stem to the end effector coupler, the tool lock comprising: a keyed opening extending through the distal end proximally into the distal portion, the keyed opening configured to receive the tool stem therein; a pin bore extending through the distal end proximate to the keyed opening; a pin disposed in the pin bore and extendable from the pin bore to engage and retain the tool stem when the tool stem is inserted into the keyed opening; a biasing element located in the pin bore and engaging the pin to bias the pin to extend from the distal end; and a pin release comprising an actuator extending beyond an external surface of the body and engaging the pin, the pin release operable to retract the pin into to the body to disengage the pin from the tool stem allowing release of the tool stem from the keyed opening.

In Example 49, the subject matter of Example 48 optionally includes wherein the pin limits rotation of the stem relative to the keyed opening to prevent release of the stem from the keyed opening when the pin engages the stem.

Example 50 is a surgical system arm system comprising: a surgical arm positionable in space and operable to lock a position of the surgical arm in a desired position, the surgical arm including a distal coupler coupled to a distal portion of the surgical arm, the distal coupler comprising a w-shaped bore extending proximally into the distal coupler from a distal end of the distal coupler.

In Example 51, the subject matter of Example 50 optionally includes an end effector coupler configured to receive and retain a tool stem therein, the end effector coupler comprising: an end effector body comprising a proximal portion and an opposite distal portion, the distal portion including a distal end; and a proximal coupler connected to the proximal portion and releasably couplable to the surgical arm.

In Example 52, the subject matter of any one or more of Examples 50-51 optionally include wherein the proximal coupler includes a protrusion having a profile that is substantially W-shaped, the protrusion insertable into the bore of the distal coupler to secure the end effector coupler to the surgical arm.

In Example 53, the system, device, or method of any one of or any combination of Examples 1-52 is optionally configured such that all elements or options recited are available to use or select from.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A system for a surgical arm, the system comprising:
a body comprising a proximal portion and an opposite distal portion, the distal portion including a distal end;
a control device couplable to an external surface of the body and operable to transmit a signal to allow movement of the surgical arm;
a coupler connected to the proximal portion and releasably couplable to the surgical arm, the coupler including a circumferential groove on an outer face of the coupler;
a tool lock for releasably retaining a tool stem to the body, the tool lock comprising:
a keyed opening extending through the distal end into the distal portion, the keyed opening configured to receive the tool stem therein;
a pin bore extending through the distal end proximate to the keyed opening;
a pin disposed in the pin bore and extendable from the pin bore to engage and retain the tool stem when the tool stem is inserted into the keyed opening; and
a biasing element located in the pin bore and engaging the pin to bias the pin to extend from the distal end; and
a pin release comprising an actuator extending beyond an external surface of the body and engaging the pin, the pin release operable to retract the pin into to the body to disengage the pin from the tool stem allowing release of the tool stem from the keyed opening.

2. The system of claim 1, wherein the pin limits rotation of the stem relative to the keyed opening to prevent release of the tool stem from the keyed opening when the pin engages the stem.

3. The system of claim 1, wherein the body includes a tapered bore aligned along a central axis running through the keyed opening and configured to receive the tool stem therein.

4. The system of claim 3, wherein the tapered bore is configured to receive a complimentary tapered section of the tool stem to form a taper-to-taper interface to limit relative motion between the body and the tool stem.

5. The system of claim 4, wherein the body includes a flat outer surface configured to receive the control device thereon and a tab channel extending through the flat outer surface.

6. The system of claim 5, wherein the control device includes a tab extending from the control device and insertable into the tab channel to releasably secure the control device to the body.

7. The system of claim 5, further comprising:
a lock extendable through the body and engageable with the pin to restrict translation of the pin relative to the bore.

8. The system of claim 7, wherein the lock extends through the flat outer surface and is displaceable into the body to release from the pin to allow the pin to translate relative to the pin bore.

9. The system of claim 8, wherein the control device is configured to engage the lock to displace the lock into the body when the control device is secured to the body.

10. The system of claim 7, wherein the pin includes a circumferential groove, and wherein the lock includes a projection engageable with the circumferential groove of the pin to restrict translation of the pin within the pin bore.

11. The system of claim 10, wherein the body includes a lock bore extending into the body substantially transverse to the pin and sized to receive the lock therein.

12. The system of claim 11, further comprising:
a lock biasing element disposed in the lock bore and engaging the lock to bias the lock to a position where the projection engages the circumferential groove of the pin.

13. An assisted surgical system comprising:
a surgical arm positionable in space when the surgical arm is unlocked;
an arm lock engageable with the surgical arm to lock the surgical arm in a desired position and to unlock the surgical arm in response to an unlock signal; and
an end effector coupler comprising:
  a body comprising a proximal portion and an opposite distal portion, the distal portion including a distal end;
  a coupler connected to the proximal portion and releasably couplable to the surgical arm;
  a keyed opening extending through the distal end into the distal portion, the keyed opening configured to secure a tool to the end effector coupler;
  a control device couplable to the end effector coupler and operable to transmit the unlock signal to unlock the surgical arm; and
  an interlock device configured to produce an interlock signal and to transmit the interlock signal in parallel to the unlock signal to allow the unlock signal to be transmitted to the arm lock when the control device is coupled to the end effector coupler.

14. The system of claim 13, wherein the interlock device includes:
a stationary component coupled to the surgical arm; and
a movable component coupled to the control device, the stationary component connectable to the movable component when the control device is coupled to the end effector coupler to complete an interlock circuit allowing the unlock signal to be transmitted to the arm lock.

15. The system of claim 13, the interlock device includes:
a stationary wireless component coupled to the surgical arm; and
a movable wireless component coupled to the end effector coupler such that the stationary wireless component and the movable wireless component can communicate wirelessly when the control device is coupled to the end effector coupler allowing the unlock signal to be transmitted to the arm lock.

16. The system of claim 13, further comprising:
an arm unlock circuit connected to the arm lock, the arm unlock circuit including an interlock switch, wherein the interlock device connects to the interlock switch to prevent the unlock signal from being delivered to the arm lock to limit movement of the surgical arm until the interlock device transmits an interlock signal to the interlock switch to complete the arm unlock circuit.

17. The system of claim 13, further comprising:
a tool movable with the surgical arm, the tool including a stem insertable into the keyed opening to secure the tool to the end effector coupler.

18. The system of claim 17, wherein the end effector coupler includes:
a pin disposed in a pin bore adjacent the keyed opening, the pin extendable from the pin bore to engage and retain the tool stem when the tool stem is inserted into the keyed opening;
a biasing element in the pin bore and engaging the pin to bias the pin to extend from the distal end; and
a pin release comprising an actuator extending beyond an external surface of the body and engaging the pin, the pin release operable to retract the pin into to the body to disengage the pin from the tool stem allowing release of the tool stem from the keyed opening.

19. The system of claim 18, wherein the stem includes a key bit extending radially from the stem, wherein the keyed opening includes a stem opening and a keyway, the stem opening configured to receive the stem therein, and the keyway extending radially from less than a full circumference of the stem opening, the keyway sized to receive the key bit therethrough to allow the end effector coupler to receive the tool stem.

\* \* \* \* \*